United States Patent
Edwards et al.

(10) Patent No.: US 11,846,919 B2
(45) Date of Patent: Dec. 19, 2023

(54) SYSTEMS, METHODS AND ARTICLES TO PROVIDE OLFACTORY SENSATIONS

(71) Applicant: VAPOR COMMUNICATIONS, INC., Cambridge, MA (US)

(72) Inventors: David A. Edwards, Boston, MA (US); Rachel Diane Field, Huntington Beach, CA (US); Amy Michelle Yin, Onalaska, WI (US); Eyal Shahar, Paris (FR)

(73) Assignee: VAPOR COMMUNICATIONS, INC., Boston, MA (US)

( * ) Notice: Subject to any disclaimer, the term of this patent is extended or adjusted under 35 U.S.C. 154(b) by 1205 days.

(21) Appl. No.: 16/208,174

(22) Filed: Dec. 3, 2018

(65) Prior Publication Data

US 2019/0339654 A1  Nov. 7, 2019

Related U.S. Application Data

(63) Continuation of application No. 14/213,683, filed on Mar. 14, 2014, now abandoned.
(Continued)

(51) Int. Cl.
*A61L 9/02* (2006.01)
*G05B 15/02* (2006.01)
(Continued)

(52) U.S. Cl.
CPC ............... *G05B 15/02* (2013.01); *A61L 9/02* (2013.01); *A61L 9/03* (2013.01); *A61L 9/035* (2013.01);
(Continued)

(58) Field of Classification Search
CPC .............. A61L 9/02; A61L 9/305; A61L 9/035
See application file for complete search history.

(56) References Cited

U.S. PATENT DOCUMENTS

| D79,717 S | 10/1929 | Hoffman |
|---|---|---|
| D99,764 S | 5/1936 | Trompeter |

(Continued)

FOREIGN PATENT DOCUMENTS

| CN | 1642583 A | 7/2005 |
|---|---|---|
| CN | 100461154 C | 2/2009 |

(Continued)

OTHER PUBLICATIONS

Maslin. Polyester, An Offbeat Comedy. New York Times May 29, 1981. (Year: 1981).*

(Continued)

*Primary Examiner* — Donald R Spamer
(74) *Attorney, Agent, or Firm* — Cozen O'Connor

(57) ABSTRACT

A scent release system includes scent cartridges containing temperature activated scent media. The scent cartridges may bear machine-readable identification that specifies which scent media are carried by the cartridge. The scent release system can be controlled by a timer to initiate a phase change of the scent media to selectively release one or more scents, followed by a reverse phase change to selectively stop release of the respective scents. A scent release system in conjunction with a mobile electronic device, such as a smart phone, allows sending and receiving scent messages. The scent release system can be built into a case for the mobile electronic device, eliminating the need for a separate unit. A private scent delivery device in the form of a headset can be worn by users of a scent release system or by scent message recipients.

19 Claims, 13 Drawing Sheets

Related U.S. Application Data

(60) Provisional application No. 61/822,270, filed on May 10, 2013, provisional application No. 61/817,180, filed on Apr. 29, 2013, provisional application No. 61/792,716, filed on Mar. 15, 2013.

(51) Int. Cl.
*H04M 1/21* (2006.01)
*A61L 9/03* (2006.01)

(52) U.S. Cl.
CPC ......... *H04M 1/21* (2013.01); *A61L 2209/133* (2013.01); *A61L 2209/134* (2013.01)

(56) References Cited

U.S. PATENT DOCUMENTS

| | | | |
|---|---|---|---|
| D163,210 S | 5/1951 | Long | |
| D172,852 S | 8/1954 | Van Koert | |
| 2,844,469 A | 7/1958 | Daniel et al. | |
| 3,163,544 A | 12/1964 | Valyi | |
| D211,154 S | 5/1968 | Pizzurro | |
| D211,505 S | 6/1968 | Anderson | |
| D213,331 S | 2/1969 | Yutzey | |
| 3,669,313 A | 6/1972 | Marand et al. | |
| D224,882 S | 10/1972 | Alpern | |
| 3,781,164 A | 12/1973 | McCaffery | |
| D247,533 S | 3/1978 | Noyes | |
| 4,258,874 A | 3/1981 | Webinger et al. | |
| D281,281 S | 11/1985 | Matalon | |
| 4,583,686 A | 4/1986 | Martens et al. | |
| D288,713 S | 3/1987 | Darneal | |
| 4,790,479 A | 12/1988 | Matsumoto et al. | |
| D306,235 S | 2/1990 | Tamamura | |
| 4,968,456 A | 11/1990 | Muderlak et al. | |
| D315,789 S | 3/1991 | Muderlak | |
| D321,284 S | 11/1991 | Marsella et al. | |
| D326,223 S | 5/1992 | Dova | |
| D327,037 S | 6/1992 | Martineau | |
| D328,025 S | 7/1992 | Farricielli | |
| 5,170,782 A | 12/1992 | Kocinski | |
| 5,195,633 A | 3/1993 | Kaminski | |
| 5,273,690 A | 12/1993 | McDowell | |
| D349,335 S | 8/1994 | Wang | |
| D363,509 S | 10/1995 | Parekh et al. | |
| D381,515 S | 7/1997 | Haynes | |
| D389,411 S | 1/1998 | Baron | |
| 5,805,768 A | 9/1998 | Schwartz et al. | |
| 5,897,325 A | 4/1999 | Koby-Olson | |
| 5,908,158 A | 6/1999 | Cheiman | |
| D411,881 S | 7/1999 | Weick | |
| 5,967,045 A * | 10/1999 | Staiger ................ B41J 2/17556 |
| | | | 101/366 |
| D431,902 S | 10/2000 | Mellin | |
| 6,152,383 A | 11/2000 | Chen | |
| D438,608 S | 3/2001 | Chen | |
| D446,849 S | 8/2001 | Weinberg | |
| D468,626 S | 1/2003 | Joedal et al. | |
| 6,581,915 B2 | 6/2003 | Bartsch et al. | |
| D477,390 S | 7/2003 | Chen | |
| 6,654,664 B1 | 11/2003 | Chiao | |
| D496,451 S | 9/2004 | Julos et al. | |
| D496,585 S | 9/2004 | McBride et al. | |
| 6,803,987 B2 | 10/2004 | Manne | |
| D512,494 S | 12/2005 | Haranaka | |
| D513,070 S | 12/2005 | Haranaka | |
| D519,624 S | 4/2006 | Chen | |
| D525,488 S | 7/2006 | McWhorter | |
| D525,871 S | 8/2006 | Zeh et al. | |
| D527,182 S | 8/2006 | Ham | |
| D532,695 S | 11/2006 | Grant | |
| 7,201,167 B2 | 4/2007 | Fink et al. | |
| D546,688 S | 7/2007 | Verburg | |
| D548,317 S | 8/2007 | Newton et al. | |
| D548,969 S | 8/2007 | Bramley | |
| D559,434 S | 1/2008 | Morris et al. | |
| D560,018 S | 1/2008 | Morris et al. | |
| D560,788 S | 1/2008 | Farrell et al. | |
| D565,956 S | 4/2008 | Fougere et al. | |
| D574,072 S | 7/2008 | Carlson et al. | |
| 7,400,822 B2 | 7/2008 | Ruiz Ballesteros et al. | |
| D575,384 S | 8/2008 | Huang | |
| D575,859 S | 8/2008 | Scimone | |
| D575,860 S | 8/2008 | Wu | |
| D577,547 S | 9/2008 | Willat et al. | |
| D582,063 S | 12/2008 | Spangler et al. | |
| D582,534 S | 12/2008 | Conway et al. | |
| D583,450 S | 12/2008 | Choi | |
| D583,451 S | 12/2008 | Aloe et al. | |
| D583,452 S | 12/2008 | Aloe et al. | |
| D593,669 S | 6/2009 | Daelemans et al. | |
| D597,192 S | 7/2009 | Drucker et al. | |
| D601,343 S | 10/2009 | Franczyk et al. | |
| 7,610,118 B2 * | 10/2009 | Schramm ............... A63H 33/40 |
| | | | 239/69 |
| D604,099 S | 11/2009 | Mishan | |
| D611,584 S | 3/2010 | Gruenbacher et al. | |
| D611,585 S | 3/2010 | Gruenbacher et al. | |
| D613,844 S | 4/2010 | Joergensen | |
| D620,365 S | 7/2010 | Desjardins | |
| D620,742 S | 8/2010 | Lion et al. | |
| D625,398 S | 10/2010 | Choi | |
| 7,824,627 B2 | 11/2010 | Michaels et al. | |
| D632,771 S | 2/2011 | Abbondanzio et al. | |
| D633,190 S | 2/2011 | Abbondanzio et al. | |
| D633,610 S | 3/2011 | Wu | |
| D634,538 S | 3/2011 | Dumas | |
| D637,274 S | 5/2011 | Chan et al. | |
| 7,963,460 B2 | 6/2011 | Joergensen | |
| 7,976,782 B2 | 7/2011 | Matsuura et al. | |
| D643,103 S | 8/2011 | Bilko et al. | |
| 7,992,801 B2 | 8/2011 | Joergensen | |
| 8,001,962 B2 | 8/2011 | Sheiman | |
| D644,725 S | 9/2011 | Kim | |
| D646,926 S | 10/2011 | Willat et al. | |
| D647,187 S | 10/2011 | Chan et al. | |
| D647,193 S | 10/2011 | Kim | |
| 8,032,014 B2 | 10/2011 | Cheung | |
| D651,090 S | 12/2011 | Grima et al. | |
| D654,761 S | 2/2012 | Herbst | |
| D656,230 S | 3/2012 | Robinson et al. | |
| D662,201 S | 6/2012 | Edwards et al. | |
| D662,578 S | 6/2012 | Blanking et al. | |
| D662,579 S | 6/2012 | Blanking et al. | |
| D662,580 S | 6/2012 | Blanking et al. | |
| D664,446 S | 7/2012 | Edwards | |
| D672,860 S | 12/2012 | Blachford et al. | |
| 8,336,545 B2 | 12/2012 | Fink et al. | |
| D675,304 S | 1/2013 | Valentino et al. | |
| D675,309 S | 1/2013 | Freeborn et al. | |
| D675,434 S | 2/2013 | Vernall et al. | |
| D676,239 S | 2/2013 | Benoit et al. | |
| D680,637 S | 4/2013 | Blachford et al. | |
| D681,182 S | 4/2013 | Tomás Vilarara et al. | |
| D681,183 S | 4/2013 | Blachford et al. | |
| D685,608 S | 7/2013 | Bangert | |
| D686,817 S | 7/2013 | Dennis | |
| 8,485,454 B1 | 7/2013 | Irvin et al. | |
| D689,999 S | 9/2013 | Viala | |
| D696,892 S | 1/2014 | Bretillot | |
| D705,918 S | 5/2014 | Robinson et al. | |
| D715,051 S | 10/2014 | Tung et al. | |
| D716,432 S | 10/2014 | Viala et al. | |
| D716,433 S | 10/2014 | Milon et al. | |
| D720,526 S | 1/2015 | Lopez-Stout | |
| D729,369 S | 5/2015 | Viala et al. | |
| 9,573,154 B2 | 2/2017 | Bretillot et al. | |
| 9,931,425 B2 | 4/2018 | Edwards et al. | |
| 2002/0066798 A1 | 6/2002 | Laudamiel-Pellet et al. | |
| 2002/0068009 A1 | 6/2002 | Laudamiel-Pellet et al. | |
| 2002/0068010 A1 | 6/2002 | Laudamiel-Pellet et al. | |
| 2002/0069465 A1 | 6/2002 | Chute et al. | |
| 2003/0020185 A1 | 1/2003 | Cox | |
| 2003/0175148 A1 | 9/2003 | Kvietok et al. | |
| 2003/0195816 A1 | 10/2003 | Dziaba et al. | |

(56) References Cited

U.S. PATENT DOCUMENTS

| | | |
|---|---|---|
| 2003/0206834 A1 | 11/2003 | Chiao et al. |
| 2004/0040557 A1 | 3/2004 | Salter et al. |
| 2005/0062841 A1 | 3/2005 | Rivera-Cintron |
| 2005/0160789 A1 | 7/2005 | Freyer et al. |
| 2005/0195367 A1 | 9/2005 | Selander et al. |
| 2005/0227745 A1 | 10/2005 | Chiang et al. |
| 2005/0229926 A1 | 10/2005 | Fink et al. |
| 2005/0265904 A1 | 12/2005 | Hardy et al. |
| 2005/0278224 A1 | 12/2005 | Bannai et al. |
| 2006/0037970 A1 | 2/2006 | Fazzio et al. |
| 2006/0039835 A1 | 2/2006 | Nottingham et al. |
| 2006/0155225 A1 | 7/2006 | Murdock et al. |
| 2006/0196100 A1 | 9/2006 | Laudamiel-Pellet et al. |
| 2006/0249518 A1 | 11/2006 | Festa |
| 2007/0023540 A1* | 2/2007 | Selander ............ A61L 9/145 239/34 |
| 2007/0041865 A1 | 2/2007 | Ayoub et al. |
| 2007/0050083 A1 | 3/2007 | Signorelli et al. |
| 2007/0067104 A1 | 3/2007 | Mays |
| 2007/0204511 A1 | 9/2007 | Lee et al. |
| 2007/0243791 A1* | 10/2007 | Stedman ............ A63H 33/006 446/227 |
| 2007/0258849 A1 | 11/2007 | Kent |
| 2007/0262477 A1 | 11/2007 | Brown et al. |
| 2007/0267010 A1 | 11/2007 | Fink et al. |
| 2008/0187609 A1 | 8/2008 | Vail et al. |
| 2008/0245362 A1 | 10/2008 | Moessis et al. |
| 2008/0279731 A1 | 11/2008 | Goreham et al. |
| 2008/0292508 A1 | 11/2008 | Zlotnik et al. |
| 2008/0299049 A1 | 12/2008 | Stangl |
| 2009/0196930 A1 | 8/2009 | Surber et al. |
| 2010/0096409 A1 | 4/2010 | Wainwright |
| 2010/0114819 A1 | 5/2010 | Kim et al. |
| 2010/0193542 A1 | 8/2010 | Macler |
| 2010/0243754 A1* | 9/2010 | Harris ............... A61L 9/14 239/34 |
| 2010/0309434 A1 | 12/2010 | Van Schijndel et al. |
| 2011/0011394 A1 | 1/2011 | Edwards et al. |
| 2011/0024521 A1 | 2/2011 | Joergensen |
| 2011/0049266 A1 | 3/2011 | Joergensen |
| 2011/0079660 A1 | 4/2011 | Joergensen |
| 2011/0186047 A1 | 8/2011 | Lewis et al. |
| 2011/0226864 A1 | 9/2011 | Kim et al. |
| 2011/0247718 A1 | 10/2011 | Samain |
| 2011/0280767 A1 | 11/2011 | Goessens |
| 2013/0173315 A1 | 7/2013 | Dorsey |
| 2013/0304255 A1 | 11/2013 | Ratnakar |
| 2014/0081777 A1 | 3/2014 | Mastrodonato et al. |
| 2014/0216603 A1 | 8/2014 | Brown |
| 2014/0230313 A1 | 8/2014 | Elman |
| 2014/0377130 A1 | 12/2014 | Edwards et al. |
| 2015/0048178 A1 | 2/2015 | Edwards et al. |
| 2017/0070845 A1 | 3/2017 | Edwards et al. |
| 2017/0076403 A1 | 3/2017 | Edwards et al. |
| 2017/0151362 A1 | 6/2017 | Edwards et al. |
| 2017/0239428 A1 | 8/2017 | Banoun |
| 2018/0036449 A1 | 2/2018 | Edwards et al. |

FOREIGN PATENT DOCUMENTS

| | | |
|---|---|---|
| CN | 105764535 A | 7/2016 |
| DE | 100 65 545 A1 | 11/2009 |
| EP | 1 098 195 A2 | 5/2001 |
| EP | 1066850 B1 | 8/2006 |
| EP | 2771052 A2 | 9/2014 |
| EP | 2 832 375 A1 | 2/2015 |
| EP | 2968637 A2 | 1/2016 |
| EP | 2968638 A2 | 1/2016 |
| EP | 3077014 A1 | 10/2016 |
| EP | 3111414 A1 | 1/2017 |
| GB | 2469876 A | 11/2010 |
| JP | H05277188 A | 10/1993 |
| JP | H11504567 A | 4/1999 |
| JP | 2005538822 A | 12/2005 |
| JP | 2009-265453 A | 11/2009 |
| JP | 2012-198694 A | 10/2012 |
| JP | 2016522690 A | 8/2016 |
| KR | 101775389 B1 | 9/2017 |
| WO | 9731721 A1 | 9/1997 |
| WO | 02/09772 A2 | 2/2002 |
| WO | 02/09773 A2 | 2/2002 |
| WO | 02/09776 A2 | 2/2002 |
| WO | 03/077962 A2 | 9/2003 |
| WO | 2004017848 A1 | 3/2004 |
| WO | 2006/074562 A1 | 7/2006 |
| WO | 2007117675 A2 | 10/2007 |
| WO | 2008042951 A2 | 4/2008 |
| WO | 2010065744 A2 | 6/2010 |
| WO | 2011/028259 A2 | 3/2011 |
| WO | 2012/038477 A1 | 3/2012 |
| WO | 2012/101642 A2 | 8/2012 |
| WO | 2015/195548 A1 | 12/2012 |
| WO | 2013006809 A2 | 1/2013 |
| WO | 2013063119 A2 | 5/2013 |
| WO | 2014/144636 A2 | 9/2014 |
| WO | 2014/144690 A2 | 9/2014 |
| WO | 2014151329 A1 | 9/2014 |
| WO | 2015/057798 A1 | 4/2015 |
| WO | 2015/130347 A1 | 9/2015 |
| WO | 2015/130348 A1 | 9/2015 |
| WO | 2016130937 A1 | 8/2016 |
| WO | 2016179167 A1 | 11/2016 |
| WO | 2016191536 A1 | 12/2016 |
| WO | 2017023702 A1 | 2/2017 |
| WO | 2017062485 A1 | 4/2017 |
| WO | 2017100874 A1 | 6/2017 |

OTHER PUBLICATIONS

Polyester Oderama Technology. Scent Card. 1981 (Year: 1981).*

Communication pursuant to Article 94(3) in related European Application No. 12 791 597.3—1113 dated Mar. 18, 2019, in 6 pages.

International Preliminary Report on Patentability and Written Opinion from PCT Application No. PCT/US2012/061695 dated Apr. 29, 2014.

International Search Report and Written Opinion for PCT/US2018/050250 dated Mar. 11, 2019 in 15 pages.

International Search Report and Written Opinion dated Jul. 30, 2020 in PCT/US2020/027818, 16 pages.

International Search Report and Written Opinion, dated Jun. 2, 2016, for International Application No. PCT/US2016/017781, 13 pages.

International Search Report from PCT Application No. PCT/US2012/061695 dated May 22, 2013, in 7 pages.

Boehret, "Does your air freshener need an app?" *The Verge*, Apr. 27, 2016, retrieved from URL=http//www.theverge.com/2016/4/27/11514206/your-air-freshener-just-got-a-lot-smarter, downloaded May 18, 2016, 5 pages.

Chinese Office Action, dated Apr. 19, 2017, for Chinese Application No. 201480025108.4, 8 pages.

Chinese Office Action, dated Mar. 2, 2017, for Chinese Application No. 201480022939.6, 4 pages.

Edwards et al., "Systems, Methods and Articles to Provide Olfactory Sensations," Preliminary Amendment, filed Nov. 6, 2014, for U.S. Appl. No. 14/213,608, 152 pages.

Edwards et al., "Systems, Methods and Articles to Provide Olfactory Sensations," Preliminary Amendment, filed Sep. 4, 2014, for U.S. Appl. No. 14/213,608, 25 pages.

Edwards et al., "Systems, Methods and Articles to Provide Olfactory Sensations," Restriction Requirement, dated Nov. 5, 2015, for U.S. Appl. No. 14/213,608, 9 pages.

Edwards et al., "Systems, Methods and Articles to Provide Olfactory Sensations," Response to Restriction Requirement and Preliminary Amendment, filed Jan. 5, 2016, for U.S. Appl. No. 14/213,608, 7 pages.

Extended European Search Report, dated Aug. 3, 2017, for European Application No. 14853938.0-1370 / 3077014, 8 pages.

(56) References Cited

OTHER PUBLICATIONS

International Preliminary Report on Patentability, dated Aug. 30, 2016, for International Application No. PCT/US2014/060643, 8 pages.
International Preliminary Report on Patentability, dated Sep. 15, 2015, for International Application No. PCT/US2014/029132, 12 pages.
International Preliminary Report on Patentability, dated Sep. 15, 2015, for International Application No. PCT/US2014/029208, 11 pages.
International Search Report, dated Dec. 17, 2014, for corresponding International Application No. PCT/US2014/029132, 5 pages.
International Search Report, dated Feb. 3, 2015, for corresponding International Application No. PCT/US2014/060643, 3 pages.
International Search Report, dated Feb. 9, 2015, for corresponding International Application No. PCT/US2014/029208, 5 pages.
International Search Report, dated Jan. 12, 2015, for corresponding International Application No. PCT/US2014/060614, 3 pages.
International Search Report, dated Jan. 16, 2015, for corresponding International Application No. PCT/US2014/060630, 3 pages.
International Search Report, dated Sep. 21, 2015, for corresponding International Application No. PCT/US2015/035805, 3 pages.
Kulture Void, "Polyester ODORAMA technology," downloaded from http://www.kulture-void.com/motion/swelter_in_vogue/polyester.html on Sep. 18, 2017, 1 page.
Maslin, "'Polyester,' an Offbeat Comedy," The New York Times, Sunday, Sep. 17, 2017, downloaded from http://www.nytimes.com/movie/review?res=9504E3DC103BF93AA15756C0A967948260, 2 pages.
Written Opinion of the International Searching Authority, completed Dec. 17, 2014, for International Application No. PCT/US2014/029132, 11 pages.
Written Opinion of the International Searching Authority, completed Jan. 12, 2015, for International Application No. PCT/US2014/060614, 10 pages.
Written Opinion of the International Searching Authority, completed Jan. 15, 2015, for International Application No. PCT/US2014/060630, 17 pages.
Written Opinion of the International Searching Authority, completed Feb. 2, 2015, for International Application No. PCT/US2014/060643, 7 pages.
Written Opinion of the International Searching Authority, completed Feb. 9, 2015, for International Application No. PCT/US2014/2014/029208, 10 pages.
Written Opinion of the International Searching Authority, completed Sep. 9, 2015, for International Application No. PCT/US2015/035805, 8 pages.

\* cited by examiner

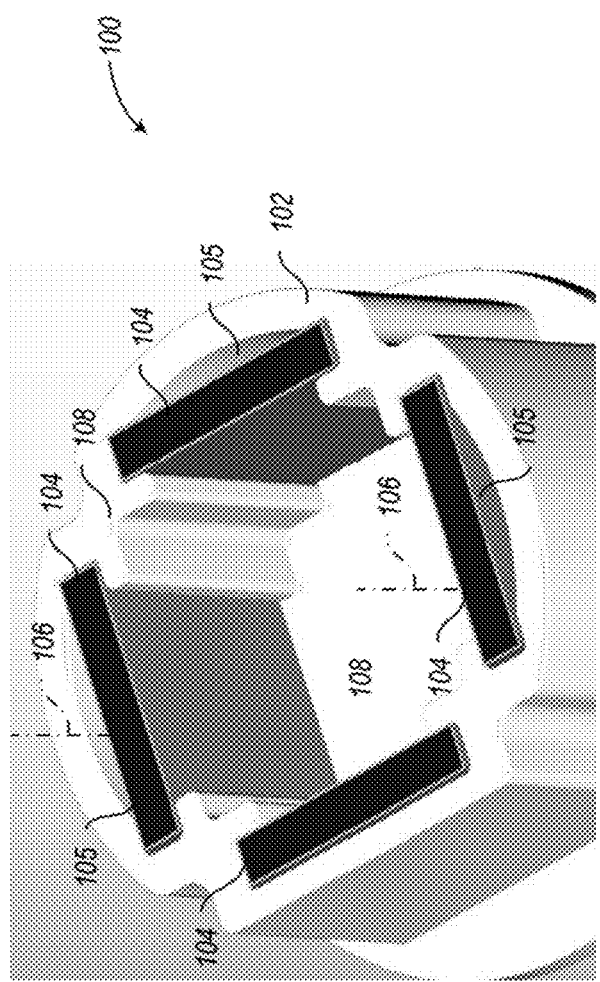
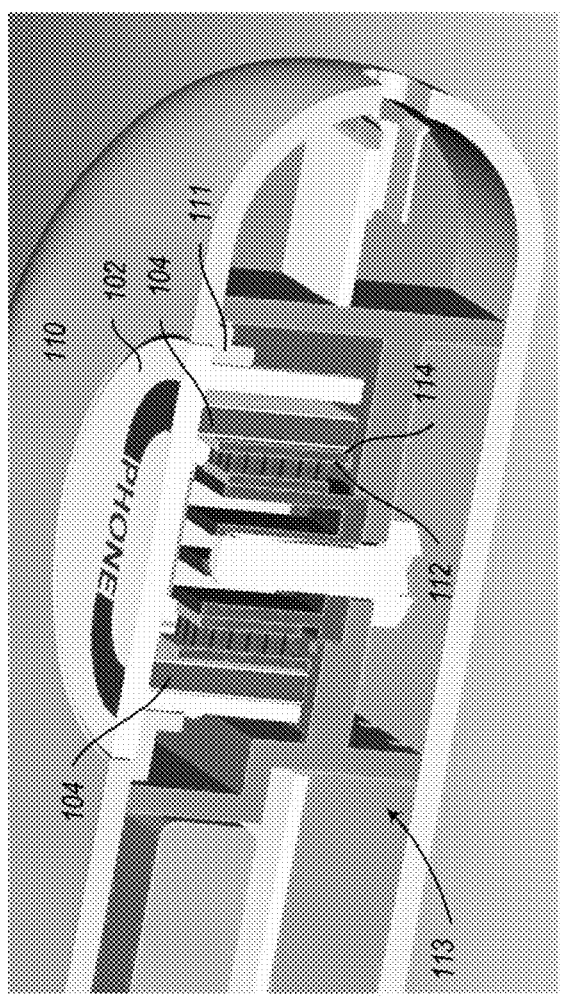
Fig. 1A
Fig. 1B

SYSTEMS, METHODS AND ARTICLES TO PROVIDE OLFACTORY SENSATIONS

BACKGROUND

Field

This disclosure generally relates to providing olfactory sensations to one or more users via a controlled system.

Description of the Related Art

All of our five senses act as messengers that deliver information to the brain, which then processes this information, causing us to respond in relatively predictable ways. Within the context of our sense of smell, all odors present themselves in specific chemical configurations, allowing humans to perceive a wide variety of distinct odors. Odor perception initiates in the nose, where the respective molecules are detected by a large family of olfactory receptors. Olfactory receptors have diverse protein sequences, and are assigned to subfamilies on the basis of sequence relationships. These observations formed the basis for research into the mechanisms underlying human odor perception, leading to the 2004 grant of the Nobel Prize in Physiology and Medicine to Linda B. Buck and Richard Axel.

However, even given the significant importance of our sense of smell, relatively little has been done to develop the apparent physiological value of this sense or to more thoroughly incorporate it into how humans experience the world around them on a daily basis. Although some systems and devices have been proposed for attempting to provide olfactory sensations to users, such systems and devices have proven inadequate as mobile, personal, targeted and effective delivery systems that may be used to alter behavior. Some of these systems and devices are intended for personal use, while other systems and devices are intended to provide olfactory sensations simultaneously to groups of people, for example people located in a common area such as a movie theater.

New approaches that selectively automate, including more precisely control and remotely deliver, desired scents, as well as coordinate audio and/or visual stimuli with olfactory sensations in order to deliver a physiological response, for personal and/or group use are desirable.

BRIEF SUMMARY

Various systems, methods, and articles are described which provide a scent sensory experience to end users. In some implementations, the system may allow the portable, discrete delivery of olfactory stimuli with audio and/or visual signals, enhancing the impact on human and animal behavior, while minimizing the impact on those not targeted by the olfactory stimuli, and thereby significantly enhancing the overall sensory experience of the user. Advantageously, such systems may be portable, allowing the user to have the benefit of the system, on demand, in a wide variety of environments. The programming of such a system can be activated by either a remote device such as a phone or other electronic equipment, or by the user. As noted above, as a complement to the programming control provided to the user, the system may also be configured to receive signals provided from a variety of devices in a remote manner, thereby allowing a third party to engage the user via olfactory stimuli in addition to audio and/or visual signals.

In other embodiments, the system may allow delivery of olfactory stimuli to a group, for example, in a theater setting, in which olfactory stimuli may enhance an audio-visual experience such as a film or a live show. Such embodiments can implement similar components and form factors to those presented below, scaled in proportion to the size of the venue or audience. Alternatively, such embodiments can employ different form factors suitable for a group setting, while maintaining consistency with the principles of operation presented herein.

The system may be used not only to enhance the overall sensory experience of the user, but, notably through the connection of the olfactory and auditory/visual signals, may be used to induce or enhance behavior change, altering physiological states. For instance, the system can deliver coffee scent which will lead to greater states of alertness. The delivery of coffee scent may be accompanied by the presentation of music and visual imagery, e.g., a coffee cup, Or the system can deliver chocolate scent, which may optionally be accompanied by the presentation of associated with images of chocolate, and promote satiety.

Furthermore, systems, methods and devices described herein allow users of electronic devices to share scents, or to advertise scents to potential consumers by communicating scent messages or scent advertisements.

A scent cartridge may be summarized as including a substrate; a plurality of temperature activated scent media carried by the substrate, the temperature activated scent media each selectively activatable to release a respective scent and to stop releasing the respective scent, the scents released by at least two of the temperature activated scent media different from one another; and at least one machine-readable identification structure physically associated with the substrate, the at least one machine-readable identification structure which provides machine-readable identification information that specifies each of the respective scents of the temperature activated scent media carried by the substrate. The at least one machine-readable identification structure may include at least one machine-readable symbol carried by at least a portion of the scent cartridge. The at least one machine-readable identification structure may include at least one wireless transponder carried by at least a portion of the scent cartridge. The at least one machine-readable identification structure may include at least one ridge or depression on the substrate. The at least one machine-readable identification structure may include at least one magnetic strip carried by the substrate. The machine-readable identification information may specify a cartridge type, each of a plurality of scent cartridges having respective temperature activated scent media that release a same combination of scents may be identified by the cartridge type. The machine-readable identification information may specify individual scents for each of the temperature activated scent media carried by the substrate.

The machine-readable identification information may further distinguish the scent cartridge from all of a plurality of other scent cartridges.

The scent cartridge may further include at least one alignment structure, the scent cartridge sized to be at least partially received in a housing, the alignment structure cooperatively interfacing with a complimentary alignment structure of the housing to at least one position to orient the temperature activated scent media in a defined orientation with respect to a set of activation elements in the housing. There may be at least four of the temperature activated scent media spatially distributed on a planar surface of the substrate in an ordered array of rows and columns to thermally conductively couple to a respective one of the activation elements of the set of activation elements, each of the temperature activated scent media having a respective major axis, each of the temperature activated scent media arranged with the respective major axis extending perpendicularly to the planar surface of the substrate. The temperature activated scent media may be arranged in a particular order according to a scent type convention.

The scent cartridge may further include a metallic foil in physical contact with at least some of the temperature activated scent media, the metallic foil thermally conductively coupling the temperature activated scent media to respective ones of the activation elements when the scent cartridge is at least partially received in the housing. The temperature activated scent media may take the form of a wax impregnated with a respective volatile, lipophilic, or oil-based scent substance.

A method of operation in a scent delivery system to provide scent from scent cartridges may be summarized as including removably receiving a scent cartridge by the scent delivery system, the scent cartridge bearing a number of scent media that selectively release respective scents; reading machine-readable information from the scent cartridge removably received by the scent delivery system; receiving a set of scent activation information by the scent delivery system, the set of scent activation information specifying a temporal sequence of scents to be released; determining by at least one processor of the scent delivery system whether the scent cartridge is appropriate for the set of scent activation information; and in response to determining that the scent cartridge is appropriate for the set of scent activation information, activating the scent media according to the set of scent activation information to provide scent from the scent delivery system.

The method may further include in response to determining that the scent cartridge is inappropriate for the set of scent activation information, providing a notification from the scent delivery system. Providing a notification from the scent delivery system may include causing a transducer of a communicatively coupled mobile electronic device to provide at least one visual, aural or tactile alert. Providing a notification from the scent delivery system may include transmitting a message to a communicatively coupled processor-based device.

The method may further include in response to determining that the scent cartridge is inappropriate for the set of scent activation information, activating the scent media in an order specified by a spatial position of the scent media in the scent cartridge that corresponds to a number of spatial positions specified by the set of scent activation information. Reading machine-readable information from the scent cartridge removably received by the scent delivery system may include optically reading at least one machine-readable symbol physically associated with the scent cartridge. Reading machine-readable information from the scent cartridge removably received by the scent delivery system may include wirelessly reading information from a wireless transponder physically associated with the scent cartridge. Reading machine-readable information from the scent cartridge removably received by the scent delivery system may include magnetically reading information from a magnetic strip physically associated with the scent cartridge. Reading machine-readable information from the scent cartridge removably received by the scent delivery system may include reading identification information that identifies a cartridge type of the scent cartridge, the cartridge type indicative of the scents releasable by all scent cartridges sharing the same cartridge type. Reading machine-readable information from the scent cartridge removably received by the scent delivery system may include reading identification information that identifies each scent releasable by the scent cartridge. Reading machine-readable information from the scent cartridge removably received by the scent delivery system may include reading identification information that distinguishes the scent cartridge from each of a plurality of other scent cartridges.

A method of operation in a scent delivery system to provide scent from removable scent cartridges may be summarized as including removably receiving a scent cartridge by the scent delivery system, the scent cartridge bearing a number of scent media, the scent media selectively transformable from a solid or semi-solid state to a liquid state and selectively transformable back to a solid or semi-solid state; receiving an indication setting a time to release at least one scent by a control subsystem; in response to an occurrence of the set time, transforming at least one of the number of scent media from the solid or semi-solid state to the liquid state to selectively release respective scents therefrom; and thereafter transforming the at least one of the number of scent media back to the solid or semi-solid state from the liquid state to selectively stop the release of respective scents therefrom. Transforming at least one of the number of the scent media from the solid or semi-solid state to the liquid state to selectively release respective scents therefrom may include heating the at least one of the number of scent media. Each of the number of scent media may include a wax substrate and at least one volatile scent material, and transforming at least one of the number of scent media from the solid or semi-solid state to the liquid state to selectively release respective scents therefrom may include heating the at least one of the number of scent media to melt the wax substrate and volatilize the volatile scent material. The scent media may include a wax substrate and the scent may be a coffee scent, and transforming at least one of the number of scent media from the solid or semi-solid state to the liquid state to selectively release respective scents therefrom may include heating the at least one of the number of scent media to melt the wax substrate and volatilize the coffee scent. Receiving an indication setting a time to release at least one scent may include receiving an indication of a wakeup time from a processor-based device, separate from and communicatively coupled with the scent delivery system.

The method may further include determining, by at least one processor, that a set time is occurring. Determining, by the at least one processor, that the first set time is occurring may include comparing the first set time to a value representative of real world time in a defined time zone. Transforming the at least one of the number of scent media back to the solid or semi-solid state from the liquid state to selectively stop the release of respective scents therefrom may include actively cooling the at least one of the number of scent media via at least one Peltier device.

A scent delivery device may be summarized as including a housing at least a portion of which is sized and dimensioned to physically removably receive at least a portion of a processor-based mobile device; the housing having at least one scent generation chamber and at least one scent media cartridge receiver that is sized and dimensioned to removably receive scent media cartridges which each carry a number of consumable scent media; and a scent actuator selectively operable to cause release of respective scents into the scent generation chamber by respective ones of a number of scent media, at least a portion of the scent delivery device communicatively coupleable to the processor-based mobile device. The housing may be a resilient silicone sleeve having at least one side wall that in use securely engages a periphery of the processor-based mobile device received in the housing. The housing may be a hard shell case having at least one side wall that in use securely engages a periphery of the processor-based mobile device received in the housing. The scent actuator may include a plurality of Peltier devices.

The scent delivery device may further include a control subsystem physically associated with the housing, the control subsystem communicatively coupled to control operation of the scent actuator.

The scent delivery device may further include a communications subsystem communicatively coupled to the control subsystem to provide communications between the control subsystem and the processor-based mobile device at least when the processor-based mobile device is received by the housing of the scent delivery device. The communications subsystem may include a radio to provide wireless communications with the processor-based mobile device. The communications subsystem may include a wired communications port to provide wireless communications with the processor-based mobile device.

The scent delivery device may further include at least one fan selectively operable to cause a flow of scent within at least one passage of the housing.

A scent delivery device may be summarized as including a support structure sized and dimensioned to be worn on a head of a biological subject; a housing physically coupled to the support structure, the housing having at least one scent generation chamber and at least one scent media cartridge receiver that is sized and dimensioned to removably receive scent media cartridges which each carry a number of consumable scent media; and a scent actuator selectively operable to cause release of respective scents into the scent generation chamber by respective ones of the number of consumable scent media, wherein at least a portion of the scent delivery device is communicatively coupleable to a processor-based mobile device. The scent actuator may include a plurality of Peltier devices.

The scent delivery device may further include a control subsystem physically associated with the housing, the control subsystem communicatively coupled to control operation of the scent actuator.

The scent delivery device may further include a communications subsystem communicatively coupled to the control subsystem to provide communications between the control subsystem and the processor-based mobile device at least when the processor-based mobile device is received by the housing of the scent delivery device. The communications subsystem may include a radio to provide wireless communications with the processor-based mobile device. The communications subsystem may include a wired communications port to provide wireless communications with the processor-based mobile device.

The scent delivery device may further include at least one fan selectively operable to cause a flow of scent within at least one passage of the housing.

The scent delivery device may further include at least one conduit having a scent port, the at least one conduit which provides a fluidly communicative path from the scent generation chamber to the scent port to selectively release scent proximate a nose of a user during use.

A method of communicating a wireless scent message containing a scent track, using a processor-based mobile device, including at least one processor and at least one non-transitory processor-readable memory communicatively coupled to the at least one processor may be summarized as including storing, by the at least one processor, a library of scent tracks in the non-transitory processor-readable memory; receiving, by the processor, a selection of a particular scent track; linking, by the processor, the scent track to a message having a text portion and a selected destination, to form the wireless scent message; and relaying, by the processor, the wireless scent message to a wireless transmitter for subsequent transmission to the selected destination. The scent track may be a pointer to a scent track that contains information to reproduce a scent sequence at the selected destination. The scent track may identify one or more consumable scent media chips that can be activated to deliver one or more scents at the selected destination. The scent track may be a machine-readable code associated with a consumable scent media chip that contains information to reproduce one or more scents at the selected destination. The wireless scent message may be formatted as one of: a short message service (SMS) message, an instant message or an electronic mail (email) message.

The method may further include displaying an icon representing the scent track; and transmitting the icon as part of the wireless scent message.

The method may further include playing an audio track representing the scent track; and transmitting the audio track as part of the wireless scent message.

A method of creating a scent message using a mobile computing device may be summarized as including selecting a scent track; selecting an icon that provides a visual representation of the scent track; and logically associating the icon and the scent track with a text message such that transmission of the text message also transmits the icon and the scent track as the scent message.

The method may further include selecting an audio track that provides an aural representation of the scent track.

The method may further include logically associating the audio track with the scent message such that transmission of the scent message also transmits the audio track.

The method may further include composing a [second?] scent track using a graphical user interface. The graphical user interface may display a graph of the audio track so as to facilitate composition of the scent track in sync with the audio track. The scent track may conform to a scent transcription protocol. The scent transcription protocol may be a MIDI protocol. The scent track may be synchronized with the audio track for coordinated playback. The scent track may be synchronized with the audio track follows structural transitions of the audio track. The structural transitions may be dynamic peaks in the audio track. The structural transitions may be structural transitions of a musical piece.

A method of receiving a wireless scent message, using a processor-based mobile device, including a processor and a non-transitory processor-readable memory communicatively coupled to the processor may be summarized as including sensing receipt of a wireless message using a wireless receiver; determining whether or not the wireless message includes a scent track; if the wireless message includes a scent track, relaying, by the processor, the wireless message from the wireless receiver to the processor-readable memory for storage in the memory as a scent message; parsing, by the processor, different components of the scent message into an icon, text, a scent track, and an audio track; in response to user input to read the scent message, displaying the text and the icon; playing the audio track; and delivering one or more scents in accordance with the scent track. The scent track may be a scent track that contains information to reproduce a scent sequence. The scent track may be a pointer to a scent track that contains information to reproduce a scent sequence. The scent track may identify one or more consumable scent media chips that can be activated to deliver one or more scents.

The method may further include alerting a user upon receipt of the scent message.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1A is a top isometric view of a portion of a scent cartridge according to one embodiment.

FIG. 1B is a cross-sectional view of a portion of a housing of a scent delivery device showing the structure of a scent cartridge receiver and a scent actuator according to one illustrated embodiment.

DETAILED DESCRIPTION

Figure 2A:
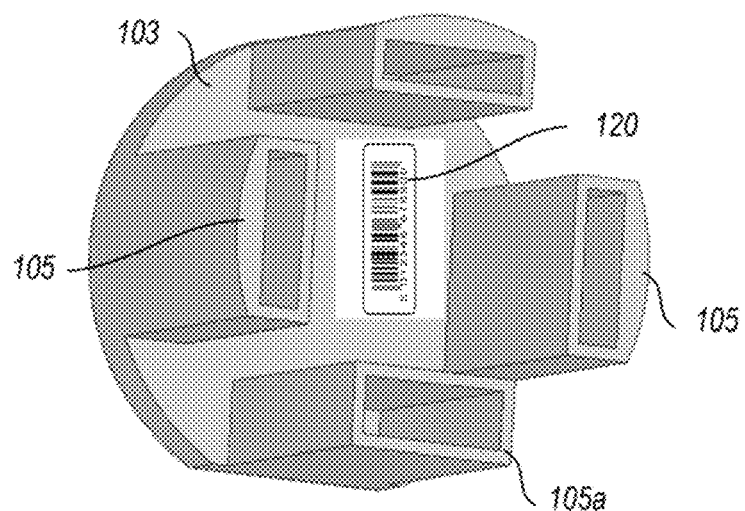
FIG. 2A is an isometric view of a scent cartridge according to one embodiment, including an optical machine-readable symbol.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with microcontrollers, Peltier devices, power supplies such as DC/DC converters, wireless radios (i.e., transmitters, receivers or transceivers), computing systems including client and server computing systems, and networks (e.g., cellular, packet switched), as well as other communications channels, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIG. 1 illustrates a scent cartridge 100, according to one embodiment. The scent cartridge 100 includes a substrate 102 having a planar surface 103 and a plurality of slots 105 containing temperature activated scent media 104 (four shown). The scent media 104 can be spatially distributed on the planar surface 103 in, for example, an ordered array of rows and columns. Each one of the temperature activated scent media 104 is oriented along a respective major axis 106 (two shown) perpendicular to the planar surface 103. While illustrated as having four chips or patches of scent media 104 per scent cartridge 100, as noted herein the scent cartridges 100 may include a greater or lesser number of scent media chips or patches. Further, the scent media 104 may be laid out or arranged on the scent cartridge 100 in any desired layout or arrangement that approximately matches or is consistent with Peltier devices or other scent release actuators.

Each of the temperature activated scent media 104 includes a substrate (e.g., a paraffin wax substrate) impregnated with at least one volatile scent material that can be selectively released from the substrate by a thermal process. Paraffin wax has a relatively low melting point and a naturally neutral scent making such an excellent choice for the scent media. The volatile scent material can be, for example, a lipophilic or oil-based scent material. The scent media 104 may take any of a large variety of forms of material capable of holding and selectively releasing scent in response to some stimulus.

The scent media 104 may be made by melting the paraffin wax and adding lipophilic scent in liquid form (e.g., essential oils). Typically, a saturation ratio of liquid scent to paraffin wax is 66-100 ml/Kg. The scent media 104 may be poured into thin sheets (e.g., 1-5 mm thick) and allowed to cool. The sheets may then be cut or otherwise divided into chips for placement on respective carriers.

The scent media 104 should also preferably be capable of stopping the release of scent in response to some stimulus, or removal of the stimulus which caused the release of scent. Stimuli may include application of heat, removal of heat, application of current, voltage, pressure, vibratory motion, or energy (e.g., ultrasonic vibration), application of electromagnetic energy (e.g., infrared light, ultraviolet light, microwaves), or even the selective rupturing, breaking, or puncturing of a membrane (e.g., self sealing membrane), blister, vial or other frangible structure.

When a selected one of the temperature activated scent media 104 is heated, the solid or semi-solid wax substrate liquefies releasing the scent and optionally volatilizing the scent material. Such a phase transformation of the substrate reverses as the melted wax cools, so that the wax substrate reverts to its former solid or semi-solid state and stops releasing scent. The cooling process can occur either passively, or through active cooling of the substrate. One or more activation elements 112 may advantageously take the form of one or more Peltier devices, as described below. Peltier devices advantageously allow both the active heating and active cooling of the temperature activated scent media 104 via the application of voltages of opposite polarities.

Typically, each of the scent media 104 carries a different scent, for example, four different coffee scents from a coffee roaster; four different perfume scents from a fragrance manufacturer; four different chocolate scents; or four unrelated scents. Alternatively, a scent cartridge 100 may contain, for example, two scent media bearing different scents and two backup scent media, since volatile materials are consumable and therefore have a finite lifetime.

Figure 2B:
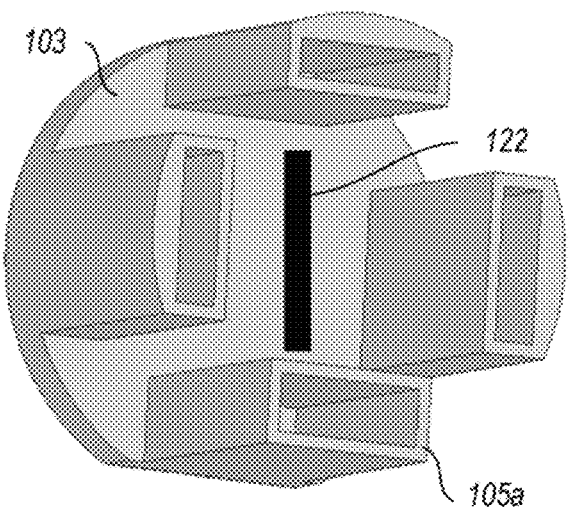
FIG. 2B is an isometric view of the scent cartridge shown in FIG. 2A, bearing a magnetic strip type.

The scent cartridge 100 is mechanically physically removably coupled to a housing 110 as shown in FIG. 1B, according to one embodiment. The scent cartridge 100 may include a scent cartridge alignment structure 108 to facilitate such coupling. The scent cartridge alignment structure 108 can cooperatively interface with a complementary alignment structure 111 within the housing 110. The alignment structures 108 and 111 then cooperate to maintain the scent cartridge 100 in a defined position or orientation with respect to a set of activation elements 112. Alignment structures 108, 111 can take the form of walls, ridges, keys, depressions, etc. with complimentary shapes. The interaction between the alignment structures 108, 111 prevents the scent cartridge from being loaded in an incorrect position or orientation. The scent cartridge 100 can be coupled to the housing 110 such that the slots 105 can be oriented vertically to ensure separation between various pieces of scent media contained within the slots 105. One embodiment of the alignment structure, as shown in FIGS. 2A and 2B, may be in the form of a unique slot 105a that has a different shape from the other slots 105, such that the scent cartridge 100 is keyed to a certain rotational orientation by the unique slot 105a. Such a key allows manufacturers of the scent cartridges 100 to distinguish the slots 105 from one another, relative to the unique slot 105a so the manufacturers can load scent media into the slots in a certain order.

The housing 110 can be a dedicated device that contains a scent chamber, as described in U.S. Provisional Patent Application Nos. 61/792,716 and 61/817,180, both of which are incorporated by reference herein, in their entireties. Alternatively, the housing 110 can be in the form of an accessory such as a cell phone case as described below, in which the case itself serves as a scent chamber. The housing 110 may take any of a large variety of shapes, and is primarily intended to provide environmental protection to the various components inside the housing. The shape of the housing 110 should not be considered limiting. Likewise, the housing 110 may be constructed of a large variety of materials. For example, the housing 110 may be formed of metal, such as aluminum. The metal may be folded, welded, and/or machined. Alternatively, the housing 110 may be formed of one or more plastics, for example an ABS or polycarbonate plastic. The plastic may be injection molded or vacuum molded to form the housing 110. The type of material or process employed to form the housing 110 from the material should not be considered limiting. The housing 110 may have a user removable cover (not shown), for example to allow the user to service one or more components. Alternatively, the housing 110 may prevent or deter user access to the internal components. The housing 110 may include a number of vents to allow cooling via convective heat transfer.

The housing 110 can include a number of ports. For example, the housing 110 can include a scent cartridge receiver 113 sized and dimensioned to removably receive the scent cartridges 100 (FIG. 1A). Alternatively, the scent cartridges 100 may be in the form of an olfactory card, and the corresponding scent cartridge receiver 113 may be in the form of a slot, similar in structure, size and/or dimension to structures used to removably receive SD cards and similar non-volatile storage media in various consumer electronics devices. The scent cartridge receiver 113 may include an ejection mechanism operable to selectively eject scent cartridges 100 from the scent cartridge receiver 113. The ejection mechanism may be similar or even identical to ejection mechanisms employed with SD card receivers found on many consumer electronics devices.

Once a scent cartridge is mounted in the scent cartridge receiver 113 of the housing 110, activation of the scent media 104 can be achieved by thermally conductively coupling the scent cartridge 100 to the activation elements 112 attached to the housing 110. The conductive coupling of the scent cartridge 100 to the activation elements 112 can optionally be enhanced by a conductive transfer layer 114 (e.g., a metal layer such as aluminum foil or copper tape) in physical contact with either or both of the temperature activated scent media 104 and the respective activation element(s) 112. The conductive transfer layer 114 permits activation to commence when the scent cartridge 100 is at least partially received in the housing 110. The conductive transfer layer 114 may thermally conductively couple the activation elements 112 (e.g., Peltier device(s)) to the scent media 104 or the scent cartridge 100.

Thus, the activation elements 112 can actively heat scent media 104 to selectively cause release of scent. For example, the activation elements 112 can heat a substrate material such as wax or other substance which contains or incorporates the scent in order to melt or partially melt such, thereby releasing scent, and optionally volatilizing the same. The activation elements 112, if implemented as Peltier devices, can also actively cool scent media 104 to selectively stop or prevent the release of scent. (Hereinafter, the terms "activation elements" and "Peltier devices" are used interchangeably, although other types of activation elements could potentially be used. In place of the Peltier devices) For example, the Peltier devices 112 may cool wax or other substance to solidify such, thereby stopping the release of scent. The Peltier devices 112 may even be turned OFF, to allow passive cooling of the scent media should that be desired. The operation of the Peltier device(s) 112 is controlled by application of a current of a first voltage to cause active heating, and a second voltage, opposite the first voltage, to cause active cooling. Peltier devices 112 may be actuated (i.e., heating, cooling) individually. Alternatively or additionally, two or more of the Peltier devices 112 may be activated concurrently (i.e., temporally overlapping at least partially in time) or even simultaneously. While the total number and spatial layout of the Peltier devices 112 can be varied in any way desired, the number of Peltier devices 112 that can be concurrently operated will depend on available power. Thus, parameters of the power source and/or power supply may limit the operation of Peltier devices 112.

Activation elements 112 may include or be thermally conductively coupled to a heat sink 116. Such facilitates transfer of heat from the Peltier device(s) 112 during cooling operation. The heat sink 116 is preferably a large thermal mass, able to quickly sink or absorb heat. The heat sink may take the form of a block of metal. Thermal paste may be employed between the surfaces of the heat sink and the Peltier devices. The heat sink 116 may include or be thermally conductively coupled to a convoluted heat transfer surface 118, having a relatively large surface area (e.g., fins, pins) as compared to its volume to facilitate convective and/or radiant heat transfer.

Figure 3A:
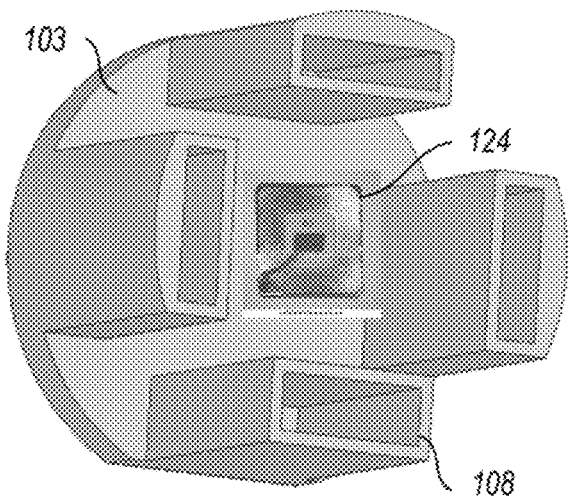
FIG. 3A is an isometric view of the scent cartridge shown in FIGS. 2A and 2B, bearing a wireless transponder.
Figure 3B:
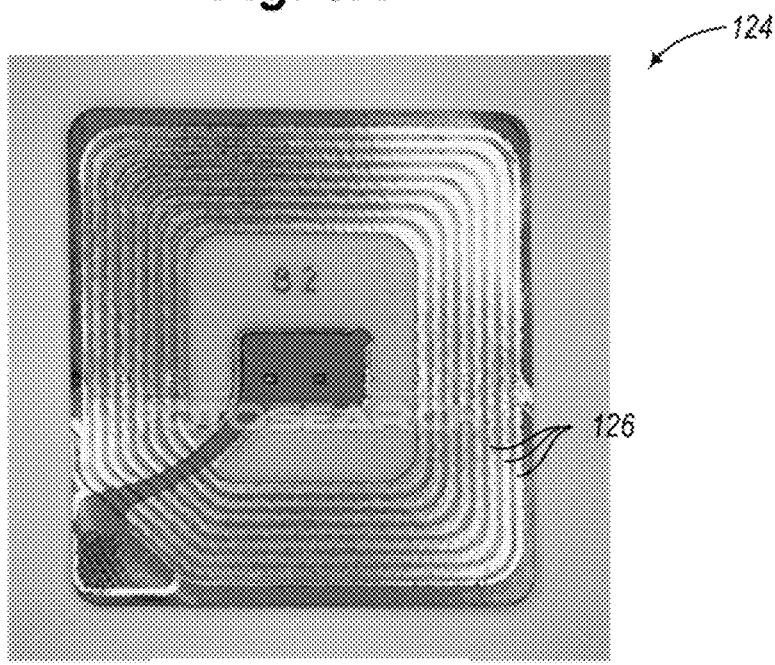
FIG. 3B is a top plan view of the wireless transponder of FIG. 3A in the form of a radio frequency identification (RFID) circuit, chip or tag.

Turning to FIG. 2A, the scent cartridge 100 can carry a machine-readable identification structure 118 on, or otherwise physically associated with, the substrate 102. For example, FIG. 2A shows the machine-readable identification structure 118 in the form of an optically readable machine-readable symbol 120 (e.g., one-dimensional or linear bar code symbol, two-dimensional area or matrix symbol). FIG. 2B shows a machine-readable identification structure 118 in the form of a magnetic strip 122. FIG. 3A shows a machine-readable identification structure 118 in the form of a wireless transponder 124, for example, a radio frequency identification (RFID) circuit, chip or tag. As shown in FIG. 3B, the wireless transducer 124 can include an integrated circuit chip 126a and an antenna 126b communicatively coupled to the integrated circuit chip 126a. Alternatively, the machine-readable identification structure 118 can be another type of machine-readable data carrier carried by at least a portion of the scent cartridge 100. For example, the scent cartridges 100 may be color coded, providing human-readable indication of the cartridge type. Thus, each type of scent cartridge 100 may be identified by a respective color (e.g., brown for coffee, red for wine, yellow for perfume). The scent delivery system may include an optical sensor or transducer (e.g., CMOS color sensor) capable of detecting and discerning between colors. The scent delivery system may optional include an illumination source (e.g., LEDs) positioned to illuminate a portion of the scent cartridge that is within a field of view of the optical sensor or transducer. Such may allow the scent delivery system to recognize or distinguish between different types of scent cartridges based on color. The type may indicate the particular scents carried by the respective scent cartridge. Thus, the color advantageously serves as both a human-readable and a machine-readable identifier.

The machine-readable identification structure 118 provides machine-readable information which identifies or allows identification of each of the respective scents of the temperature activated scent media 104. Such information can include a scent cartridge type identifier that identifies scent cartridges 100, the respective scent cartridge type (e.g., manufacturer and/or model). All scent cartridges 100 that release a same combination of scents would be identified with a common scent cartridge type identifier. For example, a vendor may mass produce scent cartridges 100 to advertise a new line of coffee flavors, wherein the scent cartridges 100 for the new line all bear the same information (e.g., in machine-readable symbol or RFID tags). Such information can differentiate a current type of scent cartridges 100 from those issued during a previous advertising campaign. Such information can differentiate scent cartridges 100 bearing coffee related scents from those bearing chocolate or wine related scents. Such information can differentiate scent cartridges 100 bearing a first combination of perfume related scents from those bearing a second combination of perfume related scents, the second combination different from the first combination. Additionally or alternatively, the machine-readable information can specify individual scents for each of the temperature activated scent media 104 contained in the scent cartridge 100. Or, the machine-readable information can uniquely identify a particular scent cartridge 100 from all other scent cartridges 100, including those of its same type.

Figure 4A:
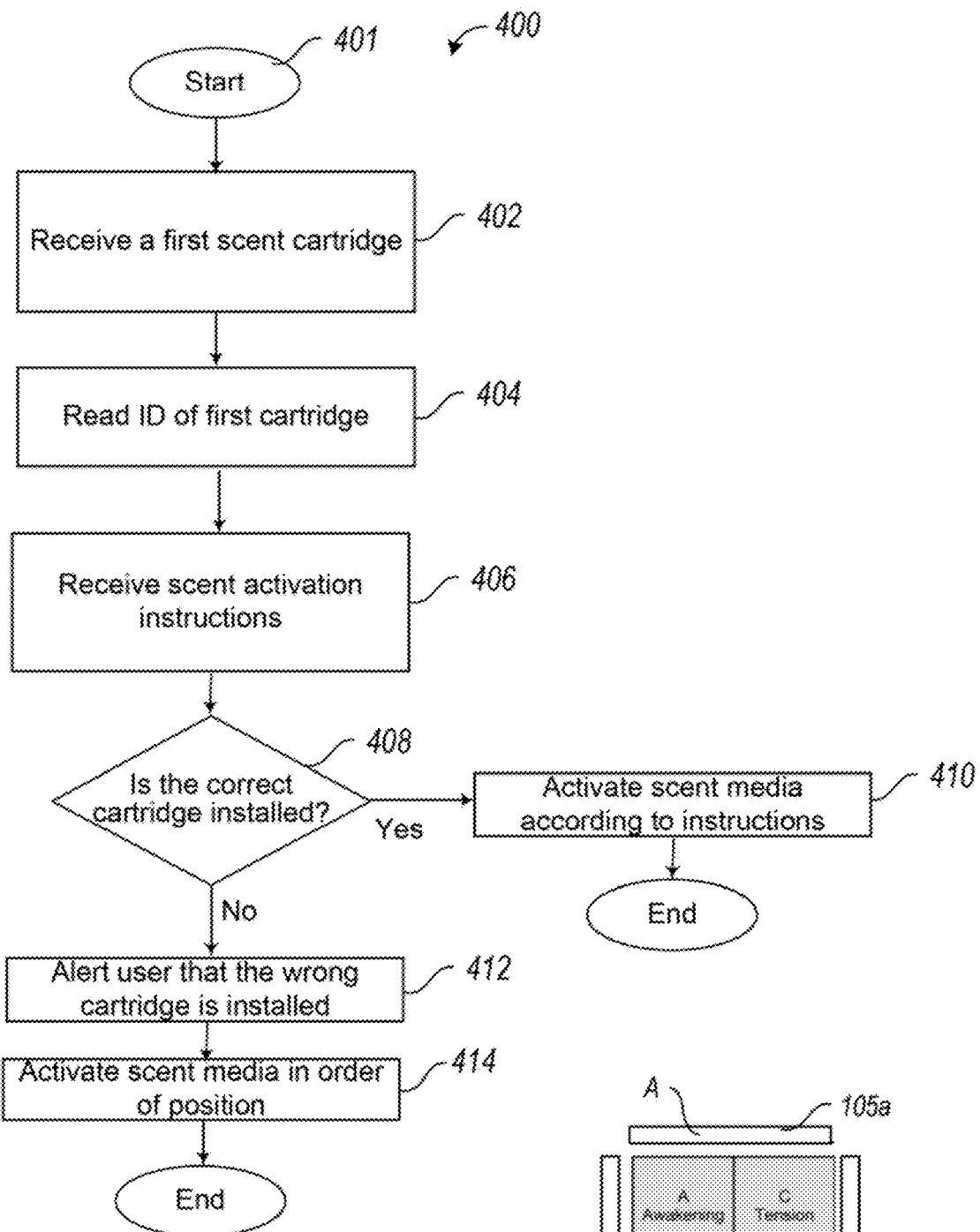
FIG. 4A is a flow diagram illustrating a method of identifying scent cartridges in a scent delivery system, according to one illustrated embodiment.

FIG. 4A shows a method of operation 400 in a scent delivery system that includes reading information from the machine-readable identification structures 118 as described above, according to one illustrated embodiment. The scent delivery system generally includes, within the housing 110, a processor-based control subsystem 128. Such a control subsystem 128 is not shown explicitly in the embodiment shown in FIG. 1B, however, the control subsystem 128 is shown below in the cell phone case embodiment illustrated in FIG. 11.

The method 400 starts at 401, for example, in response to an activation or turning ON of the scent delivery system.

At 402, a scent cartridge 100 is removably received by the scent delivery system, for example, when a user plugs the scent cartridge 100 into the scent cartridge receiver 113 on the housing 110.

At 404, a reader or other transducer reads or otherwise senses information from the machine readable ID structure 118 physically associated with the scent cartridge 100 (e.g., the wireless transponder/RFID tag 124). The information can be read by, for example, an RFID reader or interrogator, incorporated into the housing 110 of the scent delivery system. If the scent cartridge 100 bears a machine-readable symbol, an optical machine-readable symbol reader (e.g., scanning laser type, images type) provided within the housing 110 can be used to read the information. If the scent cartridge 100 bears a magnetic strip, a magnetic reader provided within the housing 110 can be used to read the magnetic strip. Applicants anticipate that any one of such exemplary types of machine-readable identification formats and associated reading hardware may become a standard for production of the scent cartridges 100 and the scent delivery system. Accordingly, embodiments are not limited to the ID format or form and associated hardware examples described above. For example, a physical shape of the scent cartridge or portion thereof may encode information. For example, a shape of a profile or periphery (e.g., round, square, hexagonal) may indicate the type of scent cartridge and hence provide some indication of the scents or types of scents carried by the scent cartridge 100. In reading the identification information carried by the ID structure 118, the reader may determine the identity of a scent cartridge type, the identity of a particular scent cartridge 100 itself, the identity of each scent releasable from the scent cartridge 100, or the identity of each piece of scent media carried by the scent cartridge 100.

At 406, the scent delivery system receives scent activation information (e.g., instructions). The scent activation information can come from an external source, for example, a mobile computing device such as a smart phone. The instructions desirably specify a scent cartridge 100 or a type of scent cartridge 100 that is recognizable by the information contained in the machine-readable identification structure 118. The instructions can also include a scent track that specifies an activation sequence for activating one or multiple different scent media 104 at selected times. The scent track can be as short as a single scent activated for a single, finite time interval or may be a long sequence of scents.

At 408, the scent delivery system determines whether or not the scent cartridge 100 installed in the scent cartridge receiver 113 is appropriate for the set of activation information. That is, whether or not the information obtained by reading the machine-readable ID structure 118 matches the one specified by the received instructions, so that the instructions for activating scents can be executed as desired or intended.

At 410, if the scent cartridge 100 is determined to be appropriate, the activation elements 112 are activated to release scent according to the scent activation instructions.

At 412, if the scent cartridge 100 is determined to be inappropriate for the scent activation information, the scent delivery system can send an alert to the user. The alert may take the form of a visual, aural, or tactile message that can be delivered via a transducer. The transducer can be part of a mobile electronic device. For example, the scent delivery system may provide notification to the user by transmitting a message to a processor-based device such as a smart phone communicatively coupled to the scent delivery system. The message can be a text message or an e-mail message. Additionally or alternatively, delivery of such a notification can cause a transducer to provide a flashing light, an alert sound, or a vibration alert, or combinations thereof. The transducer may be part of the scent delivery system or device, part of a smart phone to which the scent delivery system or device is coupled, or remote device, for instance a user's computer.

Figure 4B:
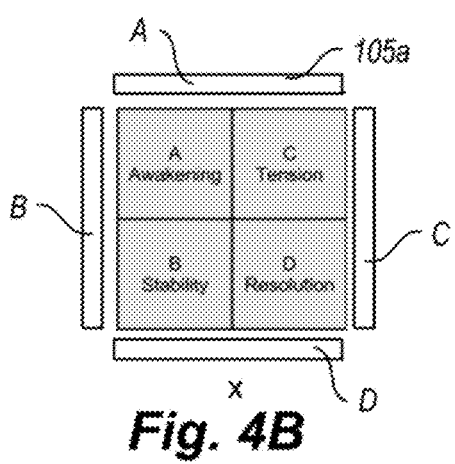
FIG. 4B is a schematic diagram showing a spatially ordered arrangement of scent media within a scent cartridge, according to one illustrated embodiment.

At 414, if the scent cartridge 100 is determined to be inappropriate for the scent activation information, additionally or in lieu of alerting the user, the scent delivery system can still activate the temperature activated scent media 104 in an order specified by a spatial position of the scent media in the scent cartridge 100. With reference to FIG. 4B, a convention can be established for production of scent cartridges wherein the scents can be categorized and placed in certain spatial positions (e.g., slots 105). For example, suppose a convention is defined such that the unique slot 105a, being generically recognizable, is designated as slot A, and the other slots, in a counter-clockwise order, are designated as B, C, and D as shown in FIG. 4B. In accordance with the convention, scents supplied with the scent cartridge 100 can be loaded into the cartridge in a certain order, according to common attributes. For example, slot A may be designated for scents that relate to "awakening," so a coffee scent (or a strongest coffee scent among four coffee scents) may be preferentially loaded into slot A. Slot B may be designated for scents that relate to "stability" (e.g., an apple pie scent), and so on. Thus, even if the intended scent cartridge 100 is not available, a scent track can be "played back" in the order specified, to approximate the intended olfactory experience. Thus, if a convention is adopted as described above, scents supplied with a similar scent cartridge, (or indeed, any scent cartridge), which are associated with similar psychological effects to those of the intended scent cartridge 101, will suffice to approximately reproduce a selected scent track.

Figure 5:
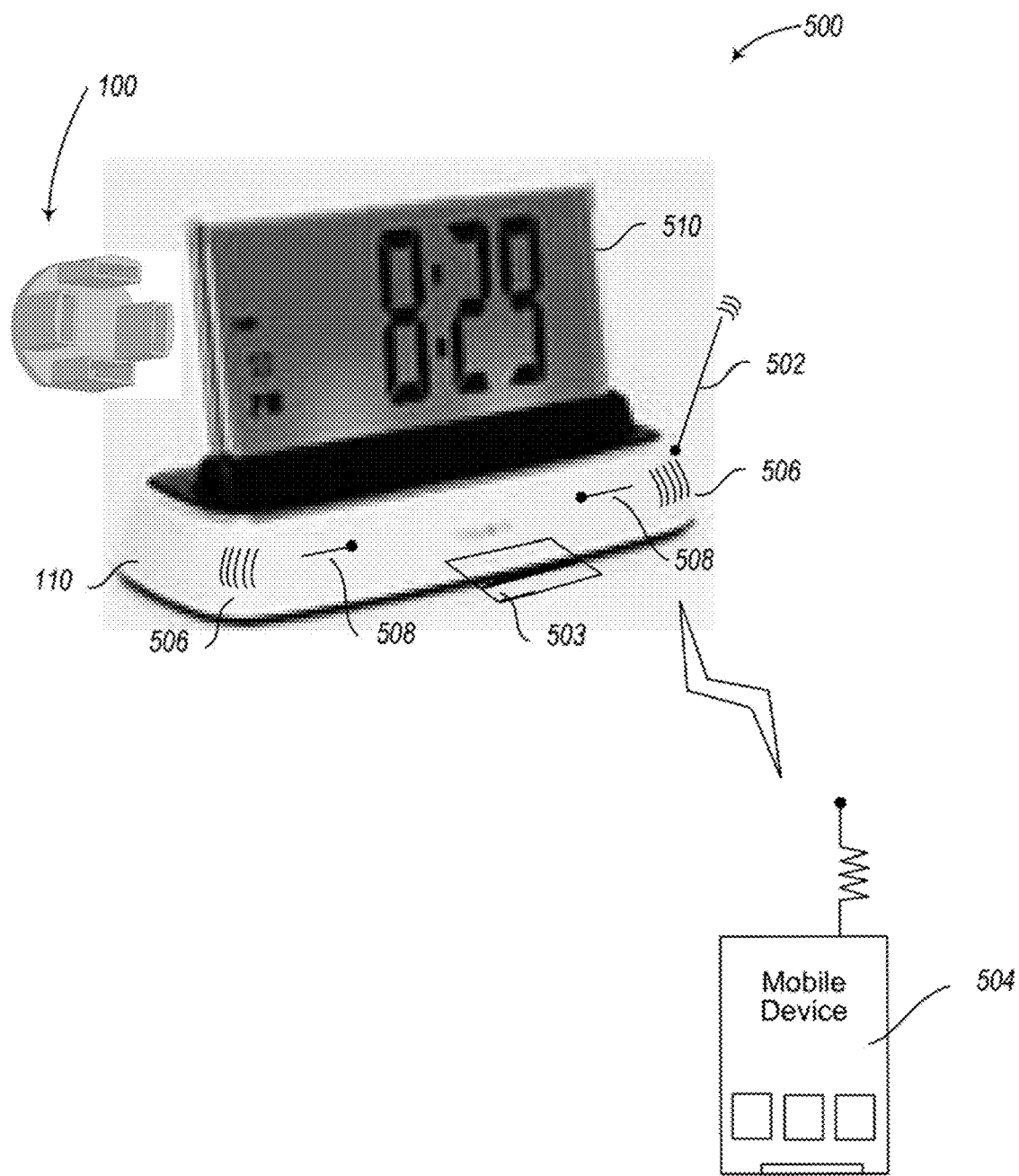
FIG. 5 is a pictorial view of a scent delivery system that in response to occurrence of a set time, for instance in lieu of an audible alarm, according to one illustrated embodiment.

FIG. 5 shows a scent delivery system according to one illustrated embodiment in which scents are released according to a timer. Such an embodiment may be referred to as a scent-based alarm clock system 500. The scent-based "alarm clock" system 500 includes the housing 110, and its internal components (e.g., the scent cartridge receiver 113 having the complimentary alignment structure 111, the activation elements 112 in the form of Peltier devices, the metallic foil 114, etc.) for receiving a scent cartridge 100, and optionally identifying the scent cartridge 100 as described above.

In one embodiment, the scent-based alarm clock system 500 includes a conventional broadcast AM/FM radio receiver indicated by the antenna 501. The scent-based alarm clock system 500 may also include a second internal wireless receiver for short range data transfer (e.g., Bluetooth™) indicated by the antenna 502. Furthermore, the scent-based alarm clock system 500 may include a docking station 503 that couples physically and electrically to a mobile electronic device 504 (e.g., smart phone or MP3 player). The mobile electronic device 504 can thus send or forward scent tracks to the scent-based alarm clock system 500 either through the docking station 503 or via the Bluetooth™ wireless path.

Exterior features of the scent-based alarm clock system 500 include vents 506 in the housing 110 to allow scents to escape the housing 110. The vents 506 may be adjustable and adjustment controls 508 may allow the vents 506 to be selectively opened and closed. The adjustable vents 506 provide fluid communication between an interior of the housing 110 and an ambient environment. Such may be used to expel or release air from the housing 110, for example after filtering scent(s) from the air. The fluid communication via the vents 506 may be selectively controllable, for example via a programmed value, for automated control, or via other structure such as the manual controls 508. In some embodiments, the vents 506 may serve as either inlet or outlet vents to either draw or expel or release air. When used as outlet vents, the adjustable vents 506 expel or release scented air to the ambient environment providing scent (e.g., intentionally scented air) to the user.

Such features, along with other components associated with the housing 110 of the scent-based alarm clock system 500, where not specified, are generally consistent with the description provided above with respect to FIGS. 1A-1B, or in the related U.S. Provisional Patent Application Nos. 61/792,716 and 61/817,180.

The scent-based alarm clock system 500 further includes a display 510 (e.g., LED, LCD), that visually displays the current "read-world" time in a given time zone in which the scent-based alarm clock system 500 is located. The scent-based alarm clock system 500 may also include conventional clock circuitry (not shown) which generally comprises a quartz movement. The display 510 has indicators or icons associated with an alarm function that includes a time-setting, and one or more alarm-setting, apparatuses (analog or digital), also consistent with alarm functions of a conventional alarm clock. The display 510 may be touch sensitive and the indicator or icon user selectable to set a time and/or alarm function or mode (e.g., scent only, scent and audible, scent and visual, scent, audible and visual, buzzer, radio, MP3 player as source of audible alarm). The display 510 is optionally physically coupled to the housing 110. The display 510 is selectively electrically coupled to the housing 110 such that an alarm condition triggers transmission of an electrical signal from the clock circuitry to the activation elements 112 of the housing 110. The display 510 and/or housing 110 may include switches and buttons selectable to set a time and/or alarm function or mode.

The scent-based alarm clock system 500 may advantageously be operated to provide scent to a user, in lieu of an audible and/or visual alarm. Alternatively, the scent may be provided in conjunction with an audible and/or visual alarm. The audible alarm may take the form of any of a variety of forms including, for example, a buzzer or tone, music or sound from an MP3 player, or sound from a broadcast source (e.g., terrestrial radio station, satellite radio).

Figure 6:
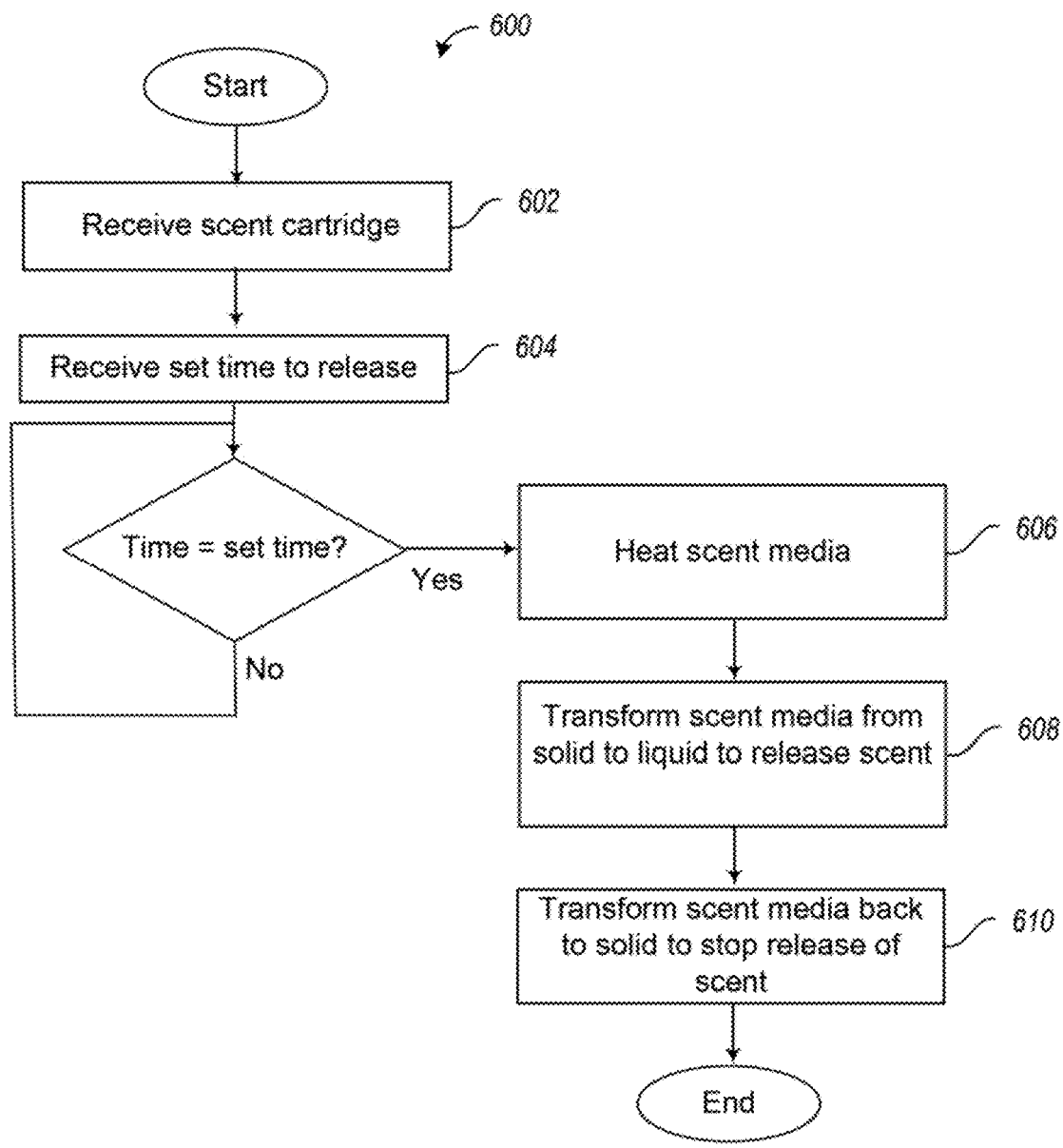
FIG. 6 is a flow diagram illustrating a method of operation of the scent delivery system of FIG. 5, according to one illustrated embodiment.

FIG. 6 shows a method of operation 600 of the scent-based alarm clock system 500, according to one illustrated embodiment.

At 602, the scent-based alarm clock system 500 receives the scent cartridge 100. For example, a user may plug the scent cartridge 100 into the scent cartridge receiver 113 of the housing 110.

While the term "alarm" is used herein, applicants note that the scent delivery is fundamentally different from conventional audible alarms. Notably, scent delivery is less jarring and a more subtle way of gaining a user's attention, whether waking a user with the aroma of freshly brewing coffee or summoning the user to a meal with the aroma of freshly baked bread or other food item.

At 604, the scent-based alarm clock system receives a set time for a scent "alarm." The scent alarm can be set manually by a user via the alarm setting apparatus. Additionally or alternatively, the scent alarm can be programmed remotely (e.g., via smart phone) and communicated via a wireless connection (e.g., Bluetooth® connection) or wired connection (e.g., via docking station). The scent alarm may or may not coincide with an audible alarm. The scent-based alarm clock system 500 may be programmed or manually set to have separate alarm conditions for a plurality of alert types, for example an audible alert (e.g., buzzer), an audio playback alarm (e.g., music), and a scent alarm.

At 605, a processor in the scent-based alarm clock system 500 determines when an alarm condition is met, for example, by comparing the clock time (e.g., a real world time in a defined time zone) against the alarm set time.

At 606, when the scent alarm condition is met, instead of, or in addition to, triggering a conventional audible wakeup alarm, an electrical signal causes heating one or more scent media 104 via scent structures (e.g., Peltier device(s)).

At 608, the heating transforms the wax substrate of at least one of the selected scent media 104 from a solid or semi-solid state through a phase transition to a liquid state. The heating may optionally volatilize the scent material. The scent is released through the vents 506. In this way, the scent alarm clock system 500 may, for example, wake a user to the aroma of, for example, freshly brewed coffee and/or cinnamon rolls. Such may be independent of whether or not there actually is any coffee or whether or not there are actually any cinnamon rolls in the near vicinity of the user.

In one embodiment, the scent alarm clock system 500 can be implemented using the mobile device 504 and a standard scent delivery system (FIG. 1B). For example, the clock timing and alarm functions are implemented via the mobile device 504 which provides signals to the scent delivery system. In still another embodiment, the scent alarm clock system 500 can be implemented using the mobile device 504 and a separate scent delivery system in the form of a mobile device case as shown below, wherein the clock timing and alarm functions are implemented via the mobile device 504.

After a time interval has elapsed, during which scent can be continuously released or released according to a scent track, cooling can begin at 610. Cooling can be passive cooling, for example when the heater is turned OFF, by simply stopping heating the temperature activated scent media 104. Alternatively, cooling can be active cooling initiated by sending a reverse polarity signal to one or more Peltier devices to actively transport heat from the temperature activated scent media 104, lowering the temperature thereof. As the temperature of the scent media 104 is lowered, the wax substrate(s) are transformed from the liquid state back to the solid or semi-solid state, thereby selectively stopping release of scent.

Figure 7:
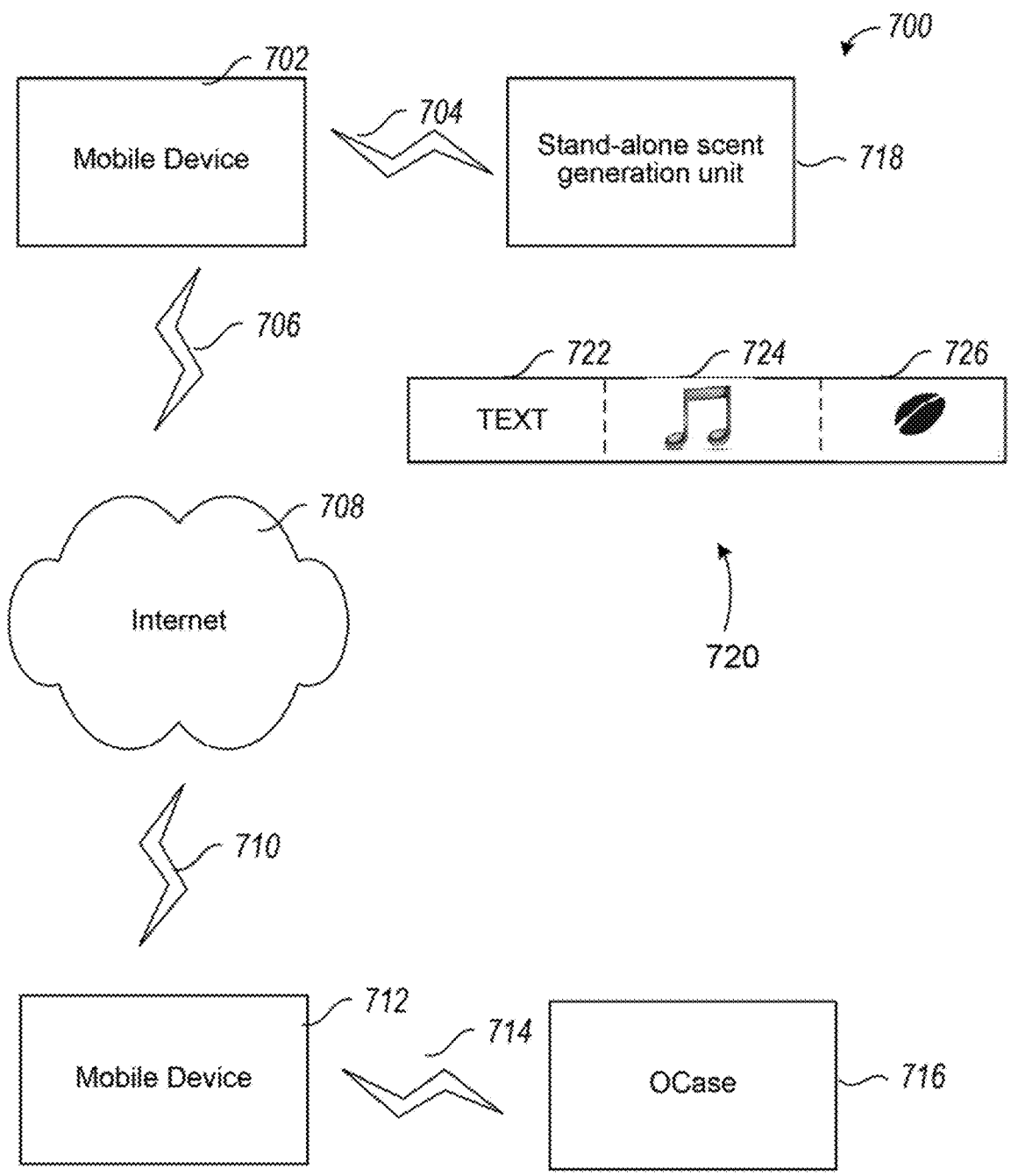
FIG. 7 is a functional block diagram showing components of a networked support system within which a pair of mobile electronic devices (e.g., smart phone) and respective scent delivery devices can engage in scent messaging, according to one illustrated embodiment.

FIG. 7 shows a scent messaging system 700 that can be used by remote users to share scents with one another, according to one illustrated embodiment. Such users may include, for example, merchants such as fragrance vendors, coffee roasters or vendors, chocolate makers or vendors, wineries or wine vendors and their existing or potential clients. According to one embodiment, the scent messaging system 700 includes mobile devices 702 and 712, each of which can communicate wirelessly with respective scent generation units 716 and 718, via wireless communication paths 704 and 714. Mobile devices 702 and 712 can also communicate wirelessly with one another via wireless communication paths 706 and 710, and a communications network (e.g., the Internet) 708.

In one embodiment, a scent message 720 can include a scent track 726. The same message 720 may also optionally include one or more of a text portion 722 and/or an audio track 724. A basic scent track 726 specifies a sequence of scents to be released by a scent delivery system (e.g., 716 or 718) at certain time intervals. The time intervals may, for example, be represented as durations or offsets from some starting time. The scent track 726 may be synchronized with the audio track 724. The scent message 720 can be stored in a nontransitory digital memory in the form of a record having multiple fields for storing the text portion 722, the audio track 724, and/or the scent track 726. Fields of the scent track 726 may specify scents, time intervals (e.g., durations, ON/OFF times), and/or temperatures. A field of the scent track 726 can generically specify a particular scent by the position in the scent cartridge 100. A field of the scent track 726 can specify the scent cartridge 100 by its machine readable ID 118.

Figure 8A:
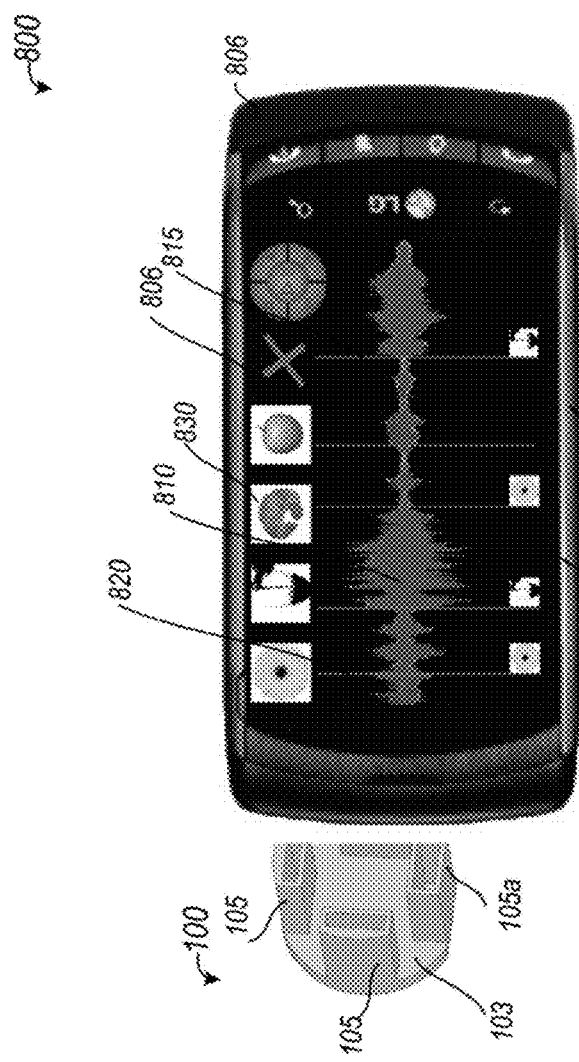
FIG. 8A is a screen shot of a mobile electronic device configured for creation of a multi-part scent message along with a portion of a scent cartridge positioned for insertion therein, according to one illustrated embodiment.
Figure 8B:
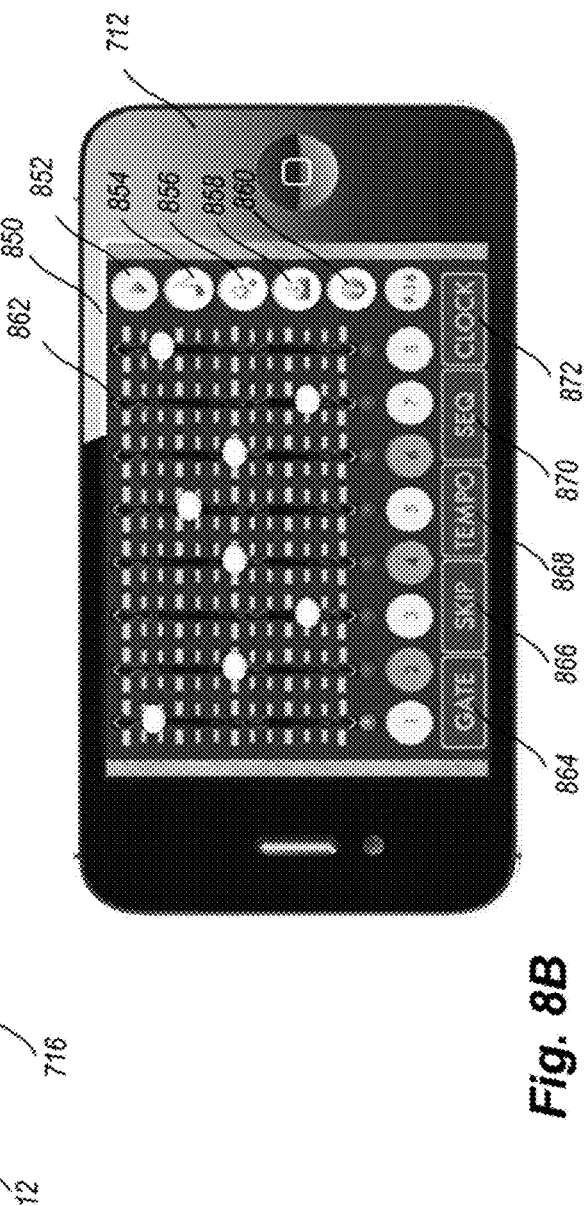
FIG. 8B is a top plan view of a mobile electronic device showing a user interface for creation of a scent sequence, according to one illustrated embodiment.

Creation of the scent message 720 using a User Interface (UI) on the mobile device 712 entails at least two of: a) composing the scent track 726, b) selecting an audio track 724, c) writing a text message 722, and/or d) specifying a recipient or destination address (e.g., email address). FIG. 8A shows a dedicated UI 800 for composition of the scent track 726 that is synchronized with the audio track 724. Such described in more detail in U.S. Provisional Patent Application Nos. 61/792,716 and 61/817,180. The UI 800 runs on the mobile device 712. The mobile device case 716 may be an "olfactory" smart phone case (e.g., hard shell, resilient silicone sleeve) that embodies the housing 110 as shown in more detail below. The UI 800 can be a simple sequencer that allows the user to associate scents to specific instances in a sound plot 810 of a song. The user might be provided with pre-calculated points of interest, such as a structural transition 815 or dynamic peaks 820 in the sound plot 810. Icons 830 representing different scents can be used as labels for the scent track composer to keep track of which scent is to be released at the various transitions in the music. The system shown in FIG. 8A can be used to test and edit a finished scent track FIG. 8B shows a mobile electronic device 712 showing a UI 850 for creation of a scent sequence, according to one illustrated embodiment.

The UI 850 includes a number of user selectable icons, selectable for example in response to a touch to implement functionality. For example, selection of a play icon 852 causes a sequence of scent, audio and/or video or visual images. The play icon 852 may toggle to a pause icon when playing. A audio icon 854 may be selected to synchornize audio and scent sequences. Selection of a send message icon 858 may send a scent message, that is an electronic message (e.g., text message, SMS message, email message) with attached or associated scent sequence information. Selection may open a dialog box to allow specification of address information where such as not previously been established for the specific scent message. Selection of an information icon 860 brings up a window or box with information. The remainder of the UI 850 is similar in some respects to a MIDI soundboard, console or mixer board, including various tracks or channels (tracks or channels 1-8 shown) with associated slides (collectively 862) to set a level, intensity or frequency of the respective track, and user selectable icons to for gating 864, skipping 866, setting tempo 868, sequencing 870 and clocking 872.

Figure 9:
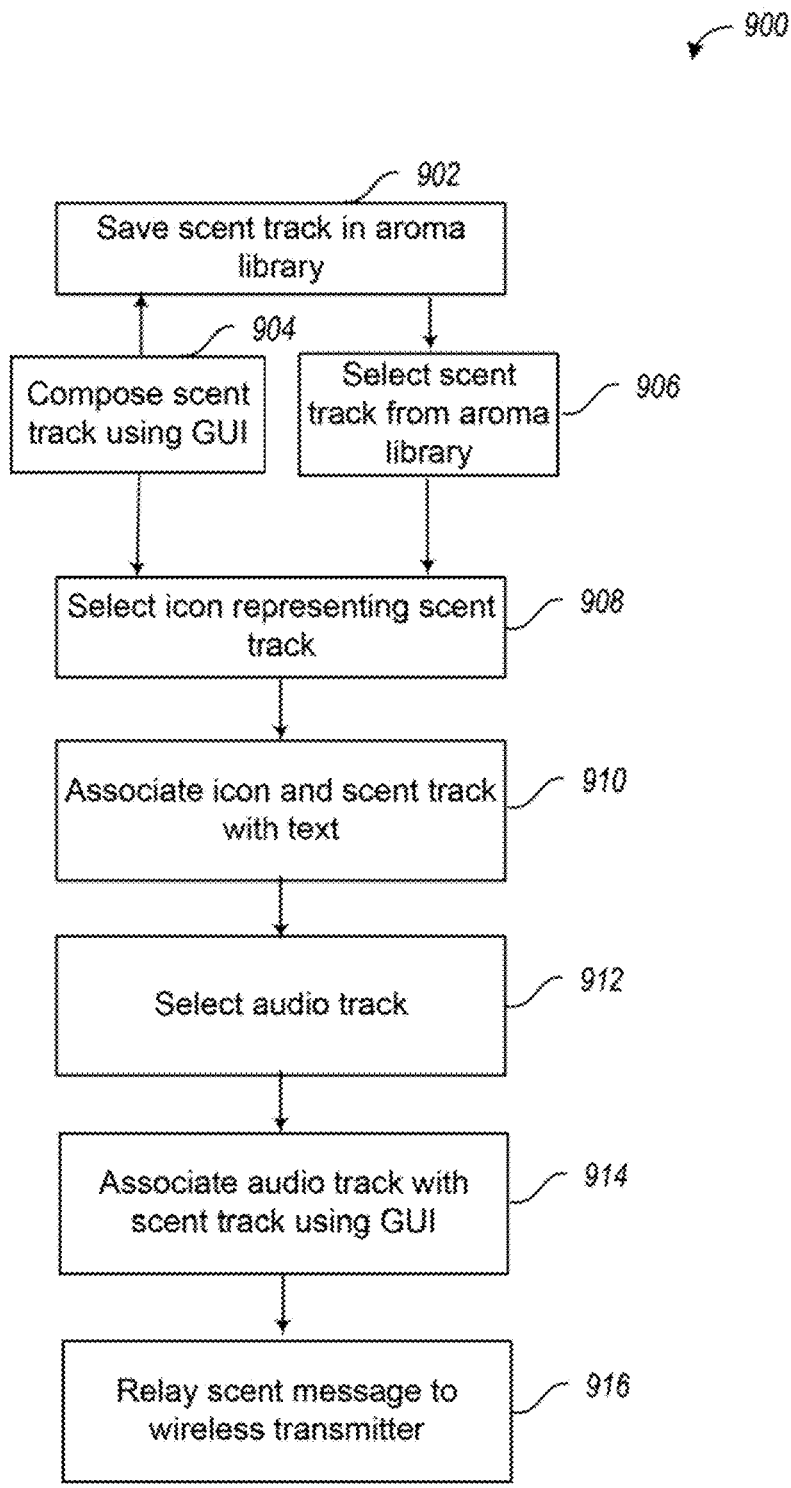
FIG. 9 is a flow diagram illustrating a method of assembling a scent message, according to one illustrated embodiment.

FIG. 9 shows a processor-implemented method 900 of assembling the scent message 720, according to one embodiment. The scent track 726 can be obtained either by creating a new one, or by selecting an existing scent track from a library of aromas. Thus, the acts 902 and 904 are optional if the desired scent track is already catalogued in the aroma library.

At 902, the processor provides tools via the UI 800 for a user to compose the scent track 726 as described above.

At 904, the processor prompts the user via the UI 800 to save the completed scent track 726 in a library of scent tracks. Alternatively, at 906, the UI 800 can present a selection of existing scent tracks from the library of scent tracks for selection of the scent track 726 by the user to be part of the scent message 720. The scent track 726 is generally in the form of a file, having a file name and a file extension such as, for example, ".stk".

At 908, the processor can present to the user via the UI 800 a selection of scent icons that can represent the scent track in place of, or in addition to, a file name and extension. For example, the coffee bean icon shown in FIG. 7 (numeral 426) can represent a scent track that causes a sequence of coffee aromas to be released. To assemble a scent message, the user can drag and drop the scent icon(s) into a text message or into an electronic mail (email) message.

At 910, the processor can logically associate a user-selected icon and the user-selected scent track 726 with a text portion 722 that has an associated address.

At 912, the processor can present to the user via the UI 800 a selection of audio tracks, for instance if the scent track was not originally created with an accompanying audio track. The user can then further assemble the scent message 720 by dragging and dropping icon(s) representing the audio track 724 into the scent message 720.

At 914, the processor can logically associate the user-selected audio track 724 with the scent track 726.

At 916, the processor relays the assembled scent message 720 to a wireless transmitter for transmission to a destination associated with the text portion 722.

The sender of a scent message need not have the capability of "playing back" the scent message, although it may be advantageous to have such capability in order to test the scent message prior to sharing the scent track with another party.

Figure 10A:
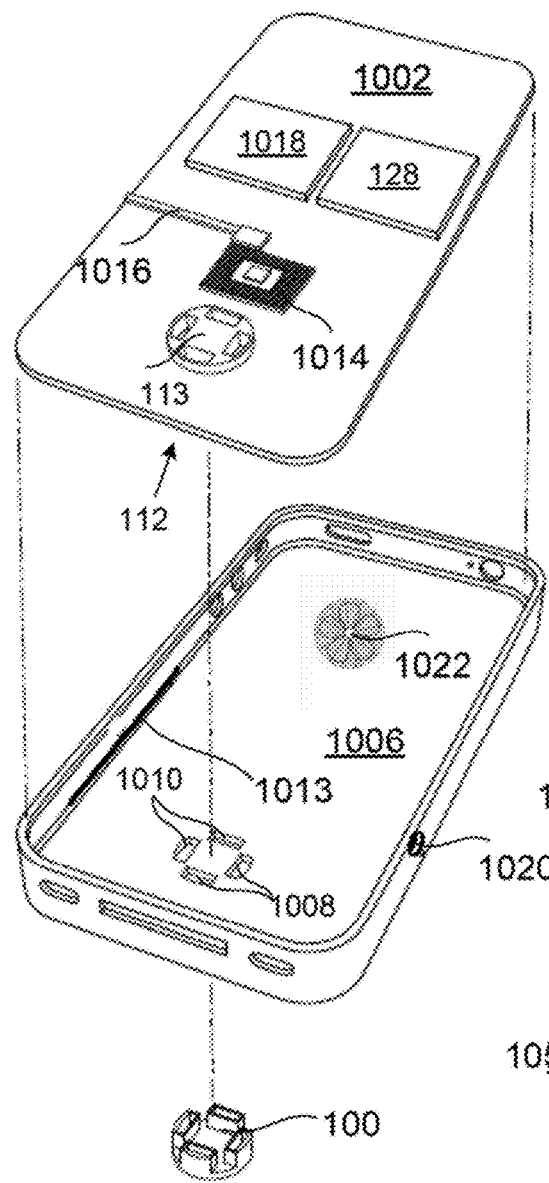
FIG. 10A is an exploded perspective view showing electronic and/or electrical components of a scent delivery device implemented as a smart phone case, according to one illustrated embodiment.
Figure 10B:
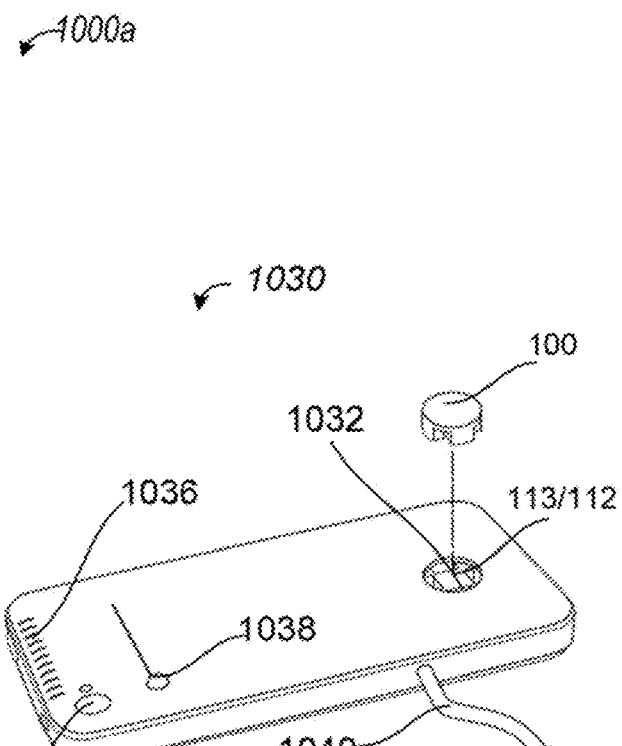
FIG. 10B is a pictorial perspective view of the underside of the scent delivery device shown in FIG. 10A.
Figure 10C:
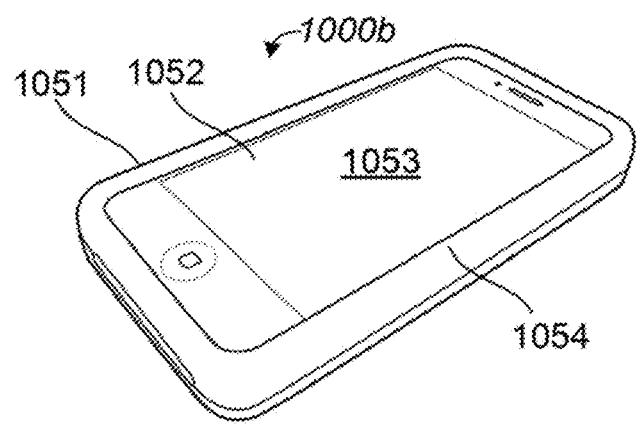
FIG. 10C is a pictorial perspective view of a mobile electronic device received in a scent delivery device which is implemented as a resilient smart phone case.

FIGS. 10A-10C illustrate scent delivery devices implemented as various embodiments of a scent delivery mobile device case 1000a-1000c. FIGS. 10A and 10B show a hard shell embodiment of a scent delivery mobile device case 1000a. In particular, circuit board 1002, normally encapsulated in a hard shell housing 1004 of the scent delivery mobile device case 1000a, is shown in FIG. 10A as having been removed from underneath an inside face plate 1006 leaving the inside face plate 1006 in the scent delivery device 1000a. The inside face plate 1006 of scent delivery mobile device case 1000a includes openings, e.g., 1008, 1010, that form the scent cartridge receiver 113. The openings 1008, 1010 accommodate external attachment of the scent cartridge 100. The openings 1008 and 1010 extend through both the back of the scent delivery mobile device case 1000a and through the circuit board 1002 so as to couple the externally-mounted scent cartridge 100 to scent activation elements 112 (e.g., Peltier devices) mounted to the circuit card 1002. When in use, the circuit board 1002 is desirably held in a slightly elevated position, suspended above the inside face plate 1006 by a circumferential ridge formed in the wall of the hard shell housing. 1004. Such a suspension creates a scent generation chamber between the underside of the circuit board 1002 and the inside face plate 1006 to receive scented air. A low-power micro-fan 1022 can be flush-mounted to the inside face plate 1006. The micro-fan 1022 can move scented air toward the vents 1036 and/or can create positive pressure within the scent generation chamber to force scented air out through the scent port 1020.

The hard shell housing 1004 of the scent delivery mobile device case 1000a can encapsulate an antenna to support wireless communication between the scent delivery mobile device case 1000a and a mobile device (not shown in FIG. 10A) disposed or received at last partially in the scent delivery mobile device case 1000. The antenna may take any of a variety of forms of, for example, a strip line radio frequency (RF) antenna 1013. The strip line RF antenna 1013, which is shown in FIG. 10A as a straight conducting element aligned with a case edge 1015, can generally assume any shape suitable for wireless communications.

The circuit board 1002 may carry various electronic and/or electrical or electrical components. For example, the circuit board 1002 may carry the control subsystem 128 and a reader or other transducer 1018 to read machine-readable identifiers 118 from the scent cartridges 100. The circuit board 2002 may additionally, or alternatively, carry an integrated circuit module 1014 and an integrated circuit module connector 1016. The integrated circuit module 1014 can include integrated circuit chips such as, for example, various types of processors (e.g., microcontrollers, microprocessors, digital signal processors), drive circuits, non-transitory processor-readable storage media, a communications subsystem including wireless receiver (e.g., radio) signal processing hardware, and decryption hardware as described below in more detail. The integrated circuit module 1014 can be electrically coupled to the control subsystem via wiring mounted on the underside of the circuit board 1002. The integrated circuit module 1014 can be a custom system-on-chip (SOC) device that serves as a platform for, and provides interconnects between, these various integrated circuits. The integrated circuit module connector 1016 provides selectable electrical coupling between the strip line RF antenna 1013 and the integrated circuit module 1014.

FIG. 10B shows a back side 1030 of the scent delivery mobile device case 1000a. The back side 1030 includes a scent cartridge opening 1032 that provides access to mount the scent cartridge 100, and a camera lens opening 1034 so as not to obstruct the cell phone camera lens. The scent delivery mobile device case 1000a also provides vents 1036 through which scented air may escape the scent generation chamber. The scent delivery mobile device case 1000a also optionally provides a sliding vent adjustment device 1038 that opens and closes the vents 1036. The sliding vent adjustment device 1038 is desirably flush or recessed slightly below the surface of the back side 1030. Also shown in FIG. 10B is a scent delivery conduit 1040 coupled to the scent port 1020. Thus, the scent delivery mobile device case 1000a allows for scented air to escape the scent generation chamber located behind the circuit board 1002 by either of two paths—through the vents 1036 or through the scent port 1020.

FIG. 10C shows a soft shell resilient embodiment of a scent delivery mobile device case 1000b in which a smart phone 1052 or other portable electronic device is placed and resiliently releasably retained. A soft case housing 1051 can be made of a pliable and/or resilient material. The soft case housing 1051 may, for example, take the form of a resilient silicone sleeve 1054. The resilient silicone sleeve 1054 serves generally to protect the smart phone 1052 from damage, for example, to cushion shocks from falls and/or prevent breakage of a standard planar display screen 1053 (e.g., touch screen). The resilient silicone sleeve 1054 may be dimensioned such that the interior dimensions of the resilient silicone sleeve 1054 are slightly smaller than the outer dimension of the smart phone 1052. Thus, the resilient silicone sleeve 1054 is stretched and retained under elastic force when the resilient silicone sleeve 1054 is attached to the smart phone 1052. While described as silicone, other elastomer or resilient materials may be used to form a suitable sleeve.

Figure 11:
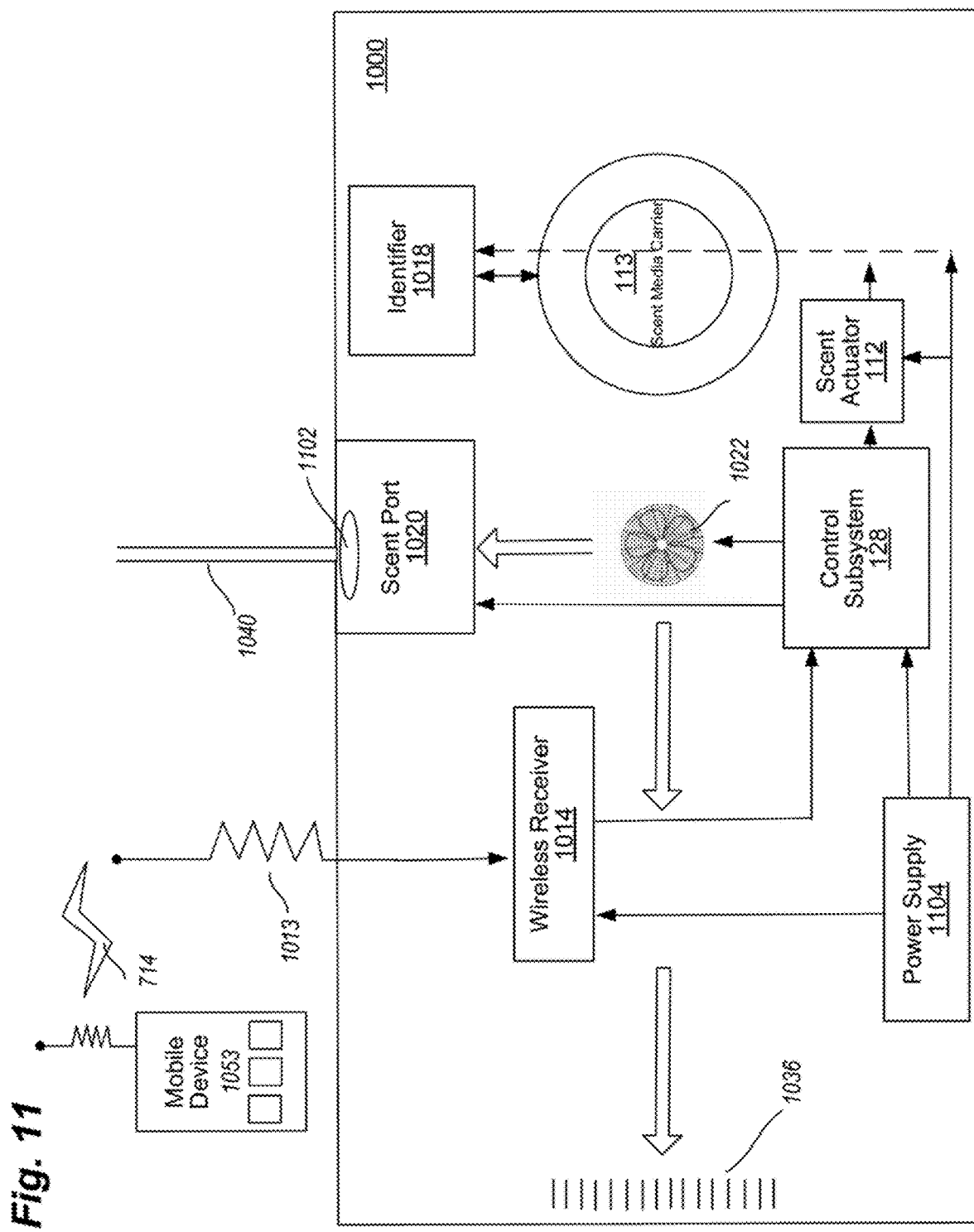
FIG. 11 is a functional block diagram showing an arrangement of, and interconnections between, electronic and/or electrical components within a scent delivery device housing, according to one illustrated embodiment.

FIG. 11 shows schematically, electronic and electrical components described above and their interconnections within the scent delivery mobile device case 1000a, 1000b.

New components not discussed above include a valve 1102 and a power supply (e.g., battery) 1104. The valve 1102 can be located at the scent port so as to prevent air from flowing from the conduit back into the scent generation chamber. The power supply 1104 provides electrical power to all of the electrical devices within the scent delivery mobile device case 1000a, 1000b. The power supply 1104 may take any of a variety of forms, for example one or more chemical battery cells (e.g., lithium ion), super- or ultra-capacitor cells and/or fuel cells. The power supply 1104 may be a rechargeable power source, for instance a secondary battery cell (e.g., nickel-cadmium, nickel-zinc, nickel metal hydride, lithium-ion) or a super- or ultra-capacitor. In such cases, the electronics may include conventional recharging circuitry. Alternatively, the power supply 1104 may be a consumable power sources such as a primary batteries (e.g., zinc-carbon, alkaline), requiring eventual replacement.

The control subsystem 128 controls the fan 1022 and the valve 1102, as well as the activation elements within the scent actuator 112. The control subsystem 128 may include a microcontroller and discrete or integrated nontransitory storage media such as memory. A suitable microcontroller may take the form of an 8-bit microcontroller with in-system programmable flash memory, such as the microcontroller commercially available from Atmel Corporation under designation ATMEGA48/88/168-AU. The microcontroller executes a program stored in its memory, and sends signals to control the various other components, for instance the activation elements 112 (e.g., Peltier devices), the fans 1022, the valve 1102, etc. Control signals may, for instance be pulse width modulated (PWM) control signal, particularly where controlling an active power supply device (e.g., DC/DC power converters). Otherwise, control signals may take on any of a large variety of forms. For instance, the microcontroller may control the fan 1022 simply by completing a circuit that powers the fan 1022. For instance, the microcontroller may control the valves 1102 simply by completing a circuit that powers the valve 1102.

Figure 12:
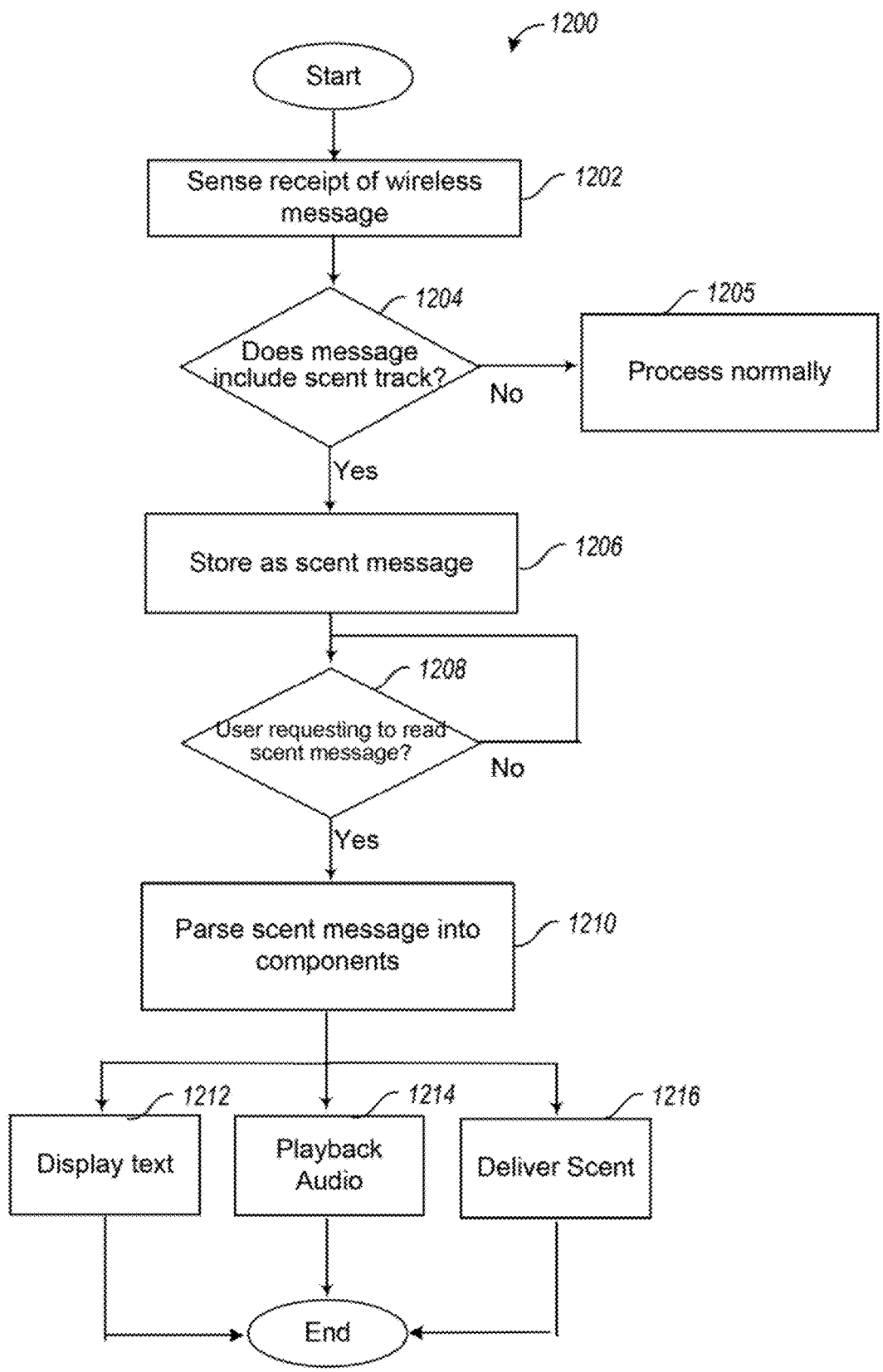
FIG. 12 a flow diagram illustrating a method of operation of a scent delivery system, according to one illustrated embodiment

As illustrated in FIG. 12, the scent delivery mobile device case 1000a, 1000b can be used, in conjunction with a mobile communication device 1053 to receive scent messages 720.

At 1202, the mobile communication device 1053 senses receipt of a wireless message.

At 1204, the mobile communication device 1053 determines whether or not the received wireless message includes a scent track and is therefore a scent message. If the message does not include a scent track, the message can be processed in the usual way, for example as a text message, SMS message, or email message.

At 1206, if it is determined that the wireless message is a scent message (i.e., includes scent specification information), the scent message can be stored prior to play back. When the mobile communication device 1053 receives an indication from the user to play back the scent message, it is necessary to engage a scent delivery system (e.g., the scent delivery mobile device case 1000a, 1000b).

At 1210, the mobile communication device 1053 parses the scent message into its component parts, for example: text, the audio and/or visual track, and the scent track.

At 1212, the text portion 722 of the scent message is displayed for the user to read.

At 1214, the audio and/or visual track 724 can be cued for substantially simultaneous playback along with the scent delivery.

At 1216, the scent track 726 can be relayed to the scent delivery system (e.g., the scent delivery mobile device case 1000a, 1000b) for execution of the encoded aroma sequence while the audio and/or visual track 724 plays in the usual way via the mobile device 1053.

Figure 13A:
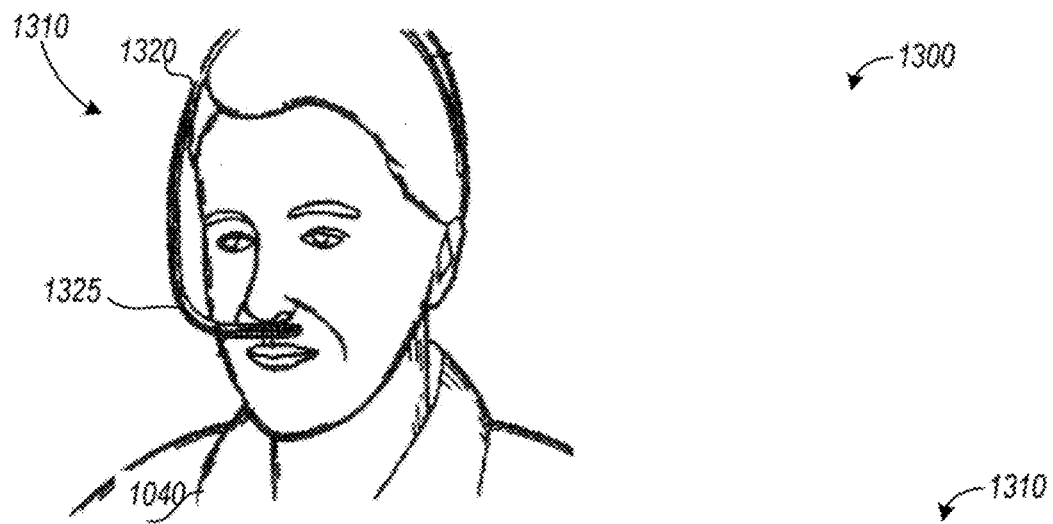
FIG. 13A is a schematic diagram of a scent delivery device worn by a user or individual, according to one illustrated embodiment.
Figure 13B:
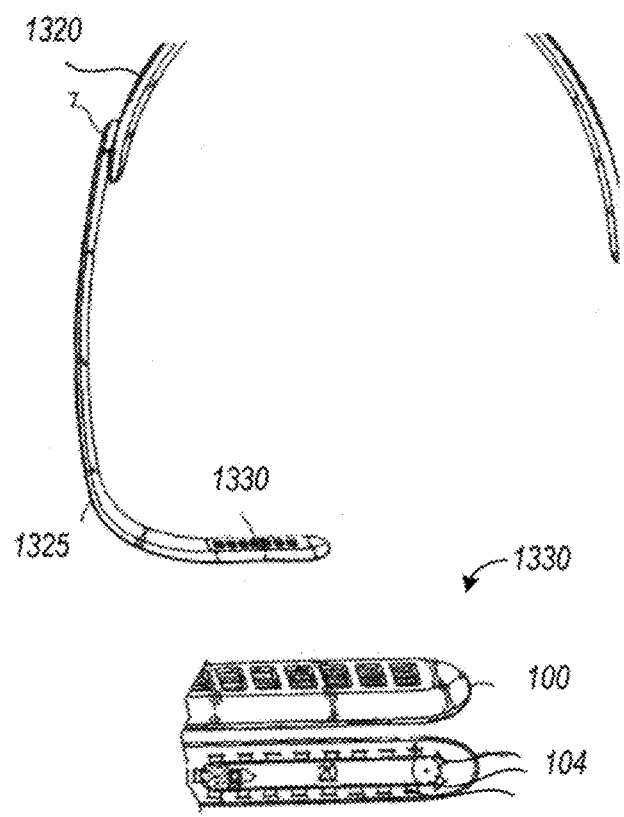
FIG. 13B is a schematic diagram with an enlarged view of the scent delivery device of FIG. 13B.

FIGS. 13A and 13B show a scent delivery system 1300 that includes a scent delivery headset 1310 in a personalized form, for delivering scent or olfactory sensation to individual users (i.e., scent consumers). The scent delivery headset 1310 includes a support structure 1320 that can be worn on the head of a user (e.g., a human being) and a scent delivery portion 1325 that extends toward the user's nose. The scent delivery headset 1310 further includes one or more headset scent delivery ports within a headset scent port module 1330 that deliver scent in proximity to a user's nose. The scent delivery system 1300 further includes a housing 110 in which scents are generated consistent with the descriptions of other embodiments above. Consistent with the description above, the housing 110 removably receives scent cartridges 100 which carry scent media 104.

In one embodiment, the scent delivery headset 1310 can be coupled to the housing 110 via one or more fluid conduits 1040. The fluid conduits 1040 may provide one or more configurable fluidly communicative paths between the headset 1310 and scent port(s) 1020 (not shown) of the housing 110 to receive scented air from inside the housing 110. The housing 110 may be in the form of the scent delivery mobile device case 1000a, 1000b, for example. One or more communications conduits within or alongside the fluid conduit 1040 may provide one or more information (e.g., instructions, data) signal paths (e.g., wires, optical fiber) between the housing 110 and the headset 1310. The headset 1310 can be coupled to one or more tensile members which may take the form of cables or alternatively strings or wires which allow the headset to be mounted on the head of the user. Employing a headset 1310 that is separate from the housing 110 allows heavier components to be separated from the headset 1310. Such facilitates a positioning of the headset scent port module 1330 located in the headset 1310 proximate a nose of the user during active use.

In one embodiment, the scent delivery headset 1310 can include the housing 110 as a self-contained unit without need of coupling via the one or more fluid conduits 1040. For example, the housing 110 can be built into the headset scent port module 1330, which can be configured as a miniaturized embodiment of the scent cartridge 100, containing the temperature activated scent media 104. Alternatively, the housing 110 can be built into the headset 1310 in the support structure 1320. The support structure 1320 can be widened at the top, for example, to accommodate components of the housing 110, or components of the housing 110 can be distributed along the support structure 1320 and/or along the scent delivery portion 1325.

The headset 1310 may optionally provide wireless communication (e.g., Bluetooth™) with the processor-based mobile device 1053. The headset 1310 may optionally provide earphones for playing audio tracks to accompany scent messages or isolated scent tracks.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary systems generally described above.

For instance, network and even non-networked topologies other than those illustrated and/or described may be employed.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays. However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various methods and/or algorithms have been described. Some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

The various embodiments described above can be combined to provide further embodiments. U.S. Provisional Patent Application No. 61/792,716, filed Mar. 15, 2013; U.S. Provisional Patent Application No. 61/817,180, filed Apr. 29, 2013; and U.S. Provisional Patent Application No. 61/822,270, filed May 10, 2013 are incorporated herein by reference, in their entireties. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation in a scent delivery system to emit scents from scent cartridges, the method comprising:
removably receiving a scent cartridge by the scent delivery system, the scent cartridge including a first plurality of scent media that selectively release respective scents;
reading machine-readable information, by at least one processor of the scent delivery system, from the scent cartridge removably received by the scent delivery system, the machine-readable information being indicative of available scent media types of the first plurality;
receiving a set of scent activation information, by at least one processor of the scent delivery system, the set of scent activation information specifying a temporal sequence of two or more scents to be released according to activation sequence for activating multiple different specified scent media at various times;

comparing, by at least one processor of the scent delivery system, the available scent media types indicated in machine-readable information against the multiple different specified scent media of the set of scent activation information before executing any portion of the temporal sequence of two or more scents to be released according to activation sequence; and in response to a determination that at least one of the multiple different specified scent media does not match any of the available scent media types as a result of the comparing, activating, by the scent delivery system, at least one scent medium from the cartridge that is with the at least one of the multiple different specified scent media that does not match any of the available scent media types.

2. The method of claim 1, further comprising:

in response to the determination that at least one of the multiple different specified scent media does not match any of the available scent media types as a result of the comparing, providing a notification from the scent delivery system.

3. The method of claim 2 wherein providing a notification from the scent delivery system includes causing a transducer of a communicatively coupled mobile electronic device to provide at least one visual, aural or tactile alert.

4. The method of claim 2 wherein providing a notification from the scent delivery system includes transmitting a message to a communicatively coupled processor-based device.

5. The method of claim 2, further comprising:

in response to a determination that the multiple different specified scent media corresponds to the available scent media types as a result of the comparing, activating, by the scent delivery system, the scent media of the cartridge according to the set of scent activation information in an order specified by a spatial position of the scent media in the scent cartridge that corresponds to a number of spatial positions specified by the set of scent activation information.

6. The method of claim 1 wherein reading machine-readable information from the scent cartridge removably received by the scent delivery system includes optically reading at least one machine-readable symbol physically associated with the scent cartridge.

7. The method of claim 1 wherein reading machine-readable information from the scent cartridge removably received by the scent delivery system includes wirelessly reading information from a wireless transponder physically associated with the scent cartridge.

8. The method of claim 1 wherein reading machine-readable information from the scent cartridge removably received by the scent delivery system includes magnetically reading information from a magnetic strip physically associated with the scent cartridge.

9. The method of claim 1 wherein reading machine-readable information from the scent cartridge removably received by the scent delivery system includes reading identification information that identifies a cartridge type of the scent cartridge, the cartridge type indicative of the scents releasable by all scent cartridges sharing the same cartridge type.

10. The method of claim 1 wherein reading machine-readable information from the scent cartridge removably received by the scent delivery system includes reading identification information that identifies each scent releasable by the scent cartridge.

11. The method of claim 1 wherein reading machine-readable information from the scent cartridge removably received by the scent delivery system includes reading identification information that distinguishes the scent cartridge from each of a plurality of other scent cartridges.

12. The method of claim 1 wherein receiving the set of scent activation information includes receiving the set of scent activation information from a device remotely located from the scent delivery system.

13. The method of claim 1 wherein receiving the set of scent activation information includes wirelessly receiving the set of scent activation information.

14. The method of claim 1 wherein the at least one processor is a processor in a scent delivery device, and wherein the set of scent activation information is based at least in part on user input received via a user interface provided by the scent delivery device.

15. The method of claim 1, wherein:

the set of scent activation information includes a scent track that indicates the activation sequence for activating the multiple different specified scent media at various times.

16. A scent delivery system comprising:

a housing;

a scent cartridge receiver; and at least one processor circuit;

wherein the scent cartridge receiver is to operatively engage with a removable scent cartridge, the scent cartridge including a first plurality of scent media that selectively release respective scents, and further including machine-readable information indicative of available scent media types of the first plurality;

wherein in operation the at least one processor circuit is to:

read the machine-readable information from the scent cartridge;

receive a set of scent activation information specifying a temporal sequence of two or more scents to be released according to activation sequence for activating multiple different specified scent media at various times;

compare the available scent media types indicated in machine-readable information against the multiple different specified scent media of the set of scent activation information before executing any portion of the temporal sequence of two or more scents to be released according to activation sequence; and in response to a determination that at least one of the multiple different specified scent media does not match any of the available scent media types as a result of the comparison, cause activation of at least one scent medium from the cartridge that is associated with the at least one of the multiple different specified scent media that does not match any of the available scent media types.

17. The scent delivery system of claim 16, wherein, in operation, the at least one processor circuit is to further:

in response to a determination that the multiple different specified scent media corresponds to the available scent media types as a result of the comparison, cause activation of at least a portion of the first plurality of scent media of the cartridge according to the set of scent activation information.

18. The scent delivery system of claim 16, wherein the set of scent activation information includes a scent track that indicates the activation sequence for activating the multiple different specified scent media at various times.

19. The scent delivery system of claim 16, wherein in response to a determination that at least one of the multiple different specified scent media does not match any of the available scent media types as a result of the comparison, initiate a notification.

* * * * *